(12) United States Patent
Miyazaki

(10) Patent No.: US 7,592,352 B2
(45) Date of Patent: Sep. 22, 2009

(54) SUBSTITUTED THIENO AND FURO-PYRIDINES

(75) Inventor: Yasushi Miyazaki, Tsukuba (JP)

(73) Assignee: SmithKline Beecham Corporation, Philadelphia, PA (US)

(*) Notice: Subject to any disclaimer, the term of this patent is extended or adjusted under 35 U.S.C. 154(b) by 437 days.

(21) Appl. No.: 10/555,796

(22) PCT Filed: Apr. 29, 2004

(86) PCT No.: PCT/US2004/013668

§ 371 (c)(1),
(2), (4) Date: Nov. 4, 2005

(87) PCT Pub. No.: WO2004/100947

PCT Pub. Date: Nov. 25, 2004

(65) Prior Publication Data

US 2008/0182868 A1    Jul. 31, 2008

Related U.S. Application Data

(60) Provisional application No. 60/468,175, filed on May 6, 2003.

(51) Int. Cl.
*A61K 31/44* (2006.01)
*C07D 513/02* (2006.01)

(52) U.S. Cl. ............... 514/301; 514/302; 546/114; 546/115

(58) Field of Classification Search ............... 546/115, 546/114; 514/301, 302
See application file for complete search history.

(56) References Cited

U.S. PATENT DOCUMENTS

| | | | |
|---|---|---|---|
| 3,492,383 A * | 1/1970 | Heimgartner ............... 264/30 |
| 6,369,227 B1 | 4/2002 | Lam et al. | |
| 7,202,363 B2 * | 4/2007 | Betschmann et al. ........ 546/114 |
| 2002/0042409 A1 | 4/2002 | Luzzio et al. | |
| 2003/0176433 A1 | 9/2003 | Beaulieu et al. | |
| 2005/0020619 A1 | 1/2005 | Betschmann et al. | |
| 2005/0026944 A1 | 2/2005 | Betschmann et al. | |
| 2005/0043347 A1 | 2/2005 | Betschmann et al. | |

FOREIGN PATENT DOCUMENTS

| | | | |
|---|---|---|---|
| JP | 07076586 | 3/1995 | |
| WO | 97/44338 | 11/1997 | |
| WO | WO98/41525 | * 9/1998 | ............... 549/513 |
| WO | 00/39108 | 7/2000 | |
| WO | 00/59902 | 10/2000 | |
| WO | 01/19828 | 3/2001 | |
| WO | 01/83472 | 11/2001 | |
| WO | 02/051849 | 7/2002 | |
| WO | 03/010141 | 2/2003 | |
| WO | 03/014377 | 2/2003 | |

* cited by examiner

*Primary Examiner*—Janet L. Andres
*Assistant Examiner*—Raymond Covington
(74) *Attorney, Agent, or Firm*—John L. Lemanowicz; Kathy Coulter

(57) ABSTRACT

This invention relates to newly identified compounds for treating and preventing tumors and cancers, and methods for treating proliferative diseases associated with the imbalance or inappropriate activity of tyrosine kinases implicated in proliferative diseases.

2 Claims, No Drawings

SUBSTITUTED THIENO AND FURO-PYRIDINES

CROSS-REFERENCE TO RELATED APPLICATIONS

This application is filed pursuant to 35 U.S.C. § 371 as a United States National Phase Application of International Application No. PCT/US2004/013668, filed Apr. 29, 2004, which claims the benefit of U.S. Provisional Application No. 60/468,175, filed May 6, 2003, now abandoned.

FIELD OF THE INVENTION

This invention relates to newly identified compounds for treating and preventing tumors and cancers, and methods for treating proliferative diseases associated with the imbalance or inappropriate activity of tyrosine kinases implicated in proliferative diseases.

BACKGROUND OF THE INVENTION

Enzymes are large proteins that catalyze reactions in living cells. Enzymes build up or tear down other molecules. For example, enzymes catalyze the synthesis of fat from fatty acids, form complex sugars from glucose and fructose, and aid in the formation of other proteins from amino acids. Enzymes also reverse the build-up process by breaking down more complex structures. Enzymes are generally specific to certain substrates for their reactions. For example, an individual enzyme may catalyze the reaction where only one substrate is involved or it may act on a group of related substrates.

Protein kinases are enzymes which catalyze the transfer of phosphorous from adenosine triphosphate (ATP), or guanosine triphosphate (GTP) to the targeted protein to yield a phosphorylated protein and adenosine diphosphate (ADP) or guanosine diphosphate (GDP), respectively. ATP or GTP is first hydrolyzed to form ADP or GDP and inorganic phosphate. The inorganic phosphate is then attached to the targeted protein. The protein substrate which is targeted by kinases may be a structural protein, found in membrane material such as a cell wall, or another enzyme which is a functional protein.

It is estimated about three to four percent of the human genome contains transcription information for the formation of protein kinases. Currently, there are about up to 400 known different protein kinases. However, because three to four percent of the human genome is a code for the formation of protein kinases, there may be many thousands of distinct and separate kinases in the human body.

Due to their physiological relevance, variety and ubiquitousness, protein kinases have become one of the most important and widely studied family of enzymes in biochemical and medical research. Studies have shown that protein kinases are key regulators of many cell functions, including signal transduction, transcriptional regulation, cell motility, and cell division. Several oncogenes have also been shown to encode protein kinases, suggesting that kinases play a role in oncogenesis.

Protein kinases are often divided into two groups based on the amino acid residue they phosphorylate. The first group, called serine/threonine kinases (PSTK), includes cyclic AMP and cyclic GMP dependent protein kinases, calcium and phospholipid dependent protein kinase, calcium and calmodulin-dependent protein kinases, casein kinases, cell division cycle protein kinases and others. These kinases are usually cytoplasmic or associated with the particulate fractions of cells, possibly by anchoring proteins. Aberrant protein serine/threonine kinase activity has been implicated or is suspected in a number of pathologies such as rheumatoid arthritis, psoriasis, septic shock, bone loss, many cancers and other proliferative diseases. Accordingly, serine/threonine kinases and the signal transduction pathways which they are part of are important targets for drug design.

The second group of kinases, called tyrosine kinases, phosphorylate tyrosine residues. They are present in much smaller quantities but also play an equally important role in cell regulation. These kinases include several receptors for molecules such as growth factors and hormones, including epidermal growth factor receptor, insulin receptor, platelet derived growth factor receptor and others. Studies have indicated that many tyrosine kinases are transmembrane proteins with their receptor domains located on the outside of the cell and their kinase domains on the inside. These transmembrane tyrosine kinases are called receptor tyrosine kinases (as opposed to non-receptor tyrosine kinases.)

Angiogenesis, the formation of new vessels from the preexisting primary plexus, occurs through several processes: vascular sprouting, branching and pruning, and the differential growth of blood vessels to form mature vascular networks. Although the cellular and molecular mechanisms underlying angiogenesis are still poorly understood, signals are transduced through endothelial cell specific molecules, particularly receptor tyrosine kinases (RTKs) and their ligands. Vascular endothelial growth factor receptors (VEGFRs), Tie receptors, and Eph receptors are primarily involved in the process of angiogenesis. Consequently, targeting of pro-angiogenic pathways is a strategy being widely pursued in order to provide new therapeutics for cancers.

Vascular endothelial growth factor (VEGF) is a peptide mitogenic for endothelial cells in vitro and stimulates angiogenic responses in vivo. VEGF has also been linked to inappropriate angiogenesis (Pinedo, H. M. et al The Oncologist, Vol. 5, No. 90001, 1-2, Apr. 2000). VEGFR(s), which are receptors for VEGF, are receptor tyrosine kinases that catalyze the phosphorylation of specific tyrosyl residues in proteins involved in the regulation of cell growth and differentiation. (A. F. Wilks, Progress in Growth Factor Research, 1990, 2, 97-111; S. A. Courtneidge, Dev. Supp. I, 1993, 57-64; J. A. Cooper, Semin. Cell Biol., 1994, 5(6), 377-387; R. F. Paulson, Semin. Immunol., 1995, 7(4), 267-277; A. C. Chan, Curr. Opin. Immunol., 1996, 8(3), 394-401). Three protein tyrosine kinase (PTK) receptors for VEGF have been identified: VEGFR-1 (Flt-1); VEGFR-2 (Flk-1 or KDR) and VEGFR-3 (Flt-4). These receptors are involved in angiogenesis and participate in signal transduction (Mustonen, T. et al J. Cell Biol. 1995:129:895-898). Of particular interest is VEGFR-2, which is a transmembrane receptor PTK expressed primarily in endothelial cells. Activation of VEGFR-2 by VEGF is a critical step in the signal transduction pathway that initiates tumor angiogenesis. VEGF expression may be constitutive to tumor cells and can also be upregulated in response to certain stimuli. One such stimuli is hypoxia, where VEGF expression is upregulated in both tumor and associated host tissues. The VEGF ligand activates VEGFR-2 by binding with its extracellular VEGF binding site. This leads to receptor dimerization of VEGFRs and autophosphorylation of tyrosine residues at the intracellular kinase domain of VEGFR-2. The kinase domain operates to transfer a phosphate from ATP to the tyrosine residues, thus providing binding sites for signaling proteins downstream of VEGFR-2 leading ultimately to initiation of angiogenesis (McMahon, G., The Oncologist, Vol. 5, No. 90001, 3-10, Apr. 2000).

Angiopoieten 1 (Ang1), a ligand for the endothelium-specific receptor tyrosine kinase TIE-2, is a novel angiogenic factor (Davis et al, Cell, 1996, 87:1161-1169; Partanen et al, Mol. Cell. Biol, 12:1698-1707 (1992); U.S. Pat. Nos. 5,521,073; 5,879,672; 5,877,020; and 6,030,831). The acronym TIE represents "tyrosine kinase containing Ig and EGF homology domains". TIE is used to identify a class of receptor tyrosine kinases, which are exclusively expressed in vascular endothelial cells and early hemopoietic cells. Typically, TIE receptor kinases are characterized by the presence of an EGF-like domain and an immunoglobulin (IG) like domain, which consists of extracellular folding units, stabilized by intrachain disulfide bonds (Partanen et al Curr. Topics Microbiol. Immunol., 1999, 237:159-172). Unlike VEGF, which functions during the early stages of vascular development, Ang1 and its receptor TIE-2 function in the later stages of vascular development, i.e., during vascular remodeling (remodeling refers to formation of a vascular lumen) and maturation (Yancopoulos et al, Cell, 1998, 93:661-664; Peters, K. G., Circ. Res., 1998, 83(3):342-3; Suri et al, Cell 87, 1171-1180 (1996)).

EphB4 is another receptor tyrosine kinase originally described in J Biol Chem as HTK (1994 May 13; 269(19):14211-8) by Bennett B D et al. The recent observation of vascular defects in ephrin-B2 and EphB4 knockout mice strongly suggests that the interaction between the ephrin-B2 ligand and its cognate EphB4 receptor defines the boundaries of arterial-venous domains. Ephrin-B2 ligands are broadly expressed in several other nonvascular tissues such as mesenchymal cells adjacent to vascular endothelial cells, but EphB4 receptors are uniquely localized in vascular endothelial cells. Not only EphB4 receptors are activated by their respective ephrin-B2 ligands, which are also transmembrane proteins, but EphB4 receptors also activate their ephrin-B2 ligands. Embryos heterozygous for EphB4 allele do not show any apparent defects in comparison to wild type. However, homozygous embryos display cardiovascular defects from endothelial cell growth retardation and arrested heart development, and embryonic lethality with high incidence. These results clearly indicate EphB4 signaling pathway plays an essential role in vasculogenesis, angiogenesis and vessel maturation, and these events are also inextricably linked to cancer and atherosclerosis.

It is also known non-receptor tyrosine kinases which are located intracellularly are involved in the transmission of biochemical signals such as those that influence tumor cell motility, dissemination and invasiveness and subsequently metastatic tumor growth. Various classes of non-receptor tyrosine kinases are known including the Src family such as Src, Lyn, Fyn and Yes tyrosine kinases, the Abl family such as Abl and Arg and the Jak family such as Jak1 and Tyk 2.

It is known that the Src family of non-receptor tyrosine kinases are highly regulated in normal cells and in the absence of extracellular stimuli are maintained in an inactive conformation. However, some Src family members, for example c-Src tyrosine kinase is frequently significantly activated (when compared to normal cell levels) in common human cancers such as gastrointestinal cancer, for example colon, rectal and stomach cancer, and breast cancer. The Src family of non-receptor tyrosine kinases has also been located in other common human cancers. It is further known that the predominant role of c-Src non-receptor kinase is to regulate the assembly of focal adhesion complexes through interaction with a number of cytoplasmic proteins including, for example, focal adhesion kinase and paxillin. In addition c-Src is coupled to signaling pathways that regulate the actin cytoskeleton which facilities cell motility. Likewise, important roles are played by the c-Src, c-Yes and c-Fyn non-receptor tyrosine kinases in integrin mediated signaling and In disrupting cadherin-dependent cell-cell junctions. Cellular motility is necessarily required for a localized tumor to progress through the stages of dissemination into the blood stream, invasion of other tissues and initiation of metastatic tumor growth. For example, colon tumor progression from localized to disseminated, invasive metastatic disease has been correlated with c-Src non-receptor tyrosine kinase activity. Accordingly it has been recognized that an inhibitor of such non-receptor tyrosine kinases should be of value as an inhibitor of the motility of tumor cells and as an inhibitor of the dissemination and invasiveness of mammalian cancer cells leading to inhibition of metastatic tumor growth. In particular an inhibitor of such non-receptor tyrosine kinases should be of value as an anti-invasive agent for use in the containment and/or treatment of solid tumor diseases.

The compounds of the present invention possess activities to one or more tyrosine kinases described herein, in particular selected from the group consisting of Tie-2, VEGFR-2, Src-c, and EphB4 proteins, implicated in cancers or atherosclerosis by inhibiting or preventing inappropriate angiogenesis, vasculogenesis, vessel maturation, or cell motilities.

SUMMARY OF THE INVENTION

In a first aspect, the instant invention relates to a compound of the formula I, or a salt, solvate, or a physiologically functional derivative thereof

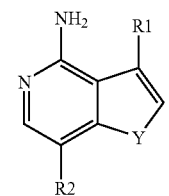

I in which Y is sulfur or oxygen;

R1 is phenyl optionally and independently substituted with one to three halogen, hydroxy, $C_{1-6}$ alkyl, $C_{1-6}$ alkyloxy, aryloxy, hydroxymethyl, —C(O)Q, —NH—C(O)NH-Q, —NHC(O)-Q, —NHSO$_2$-Q, —C(O)NH-Q, —SO$_2$NH-Q, wherein Q is hydrogen, $C_{1-6}$ alkyl, $C_{1-6}$ cycloalkyl, aryl, or aralkyl; or R1 is a radical of the formula

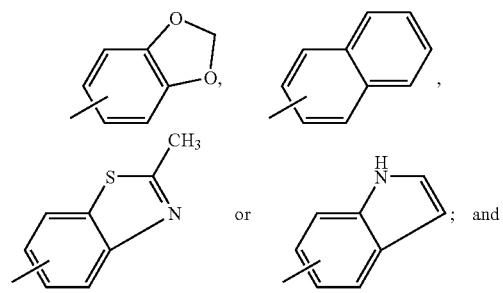

R2 is hydrogen, halogen, pyridyl, or phenyl optionally and independently substituted with one to three halogen, cyano, $C_{1-6}$alkyloxy, —C(O)-Z, —C(O)NH-Z, —SO$_2$NH-Z, —NHC(O)-Z, —NHSO$_2$-Z, —SO$_2$-Z, wherein Z is hydrogen or $C_{1-6}$alkyl.

In a second aspect, the instant invention relates to a method of inhibiting one or more tyrosine kinases selected from the group consisting of Tie-2, VEGFR-2, Src-c, and EphB4 proteins in a mammal; comprising, administering to the mammal a therapeutically effective amount of a compound of the formula I, or a salt, solvate, or a physiologically functional derivative thereof.

In a third aspect of the present invention, there is provided a pharmaceutical composition including a therapeutically effective amount of a compound of formula I, or a salt, solvate, or a physiologically functional derivative thereof and one or more of pharmaceutically acceptable carriers, diluents and excipients.

In a fourth aspect of the present invention, there is provided the use of a compound of formula I, or a salt, solvate, or a physiologically functional derivative thereof in the preparation of a medicament for use in the treatment or prevention of a disease caused by inappropriate vasculogenesis, angiogenesis, vessel maturation or cell motility, or a condition of inappropriate vasculogenesis, angiogenesis, vessel maturation or cell motility resulting from the imbalance or inappropriate activity of one or more tyrosine kinases selected from the group consisting of Tie-2, VEGFR-2, Src-c, and EphB4 proteins, including but not limited to, cancer and atherosclerosis.

In a fifth aspect, the present invention relates to a method of treating or preventing a disease caused by inappropriate vasculogenesis, angiogenesis, vessel maturation or cell motility, or a condition of inappropriate vasculogenesis, angiogenesis, vessel maturation or cell motility resulting from the imbalance or inappropriate activity of one or more tyrosine kinases selected from the group consisting of Tie-2, VEGFR-2, Src-c and EphB4 proteins including, but not limited to, cancer and atherosclerosis; comprising administering to a mammal a therapeutically effective amount of a compound of formula I, or a salt, solvate, or a physiologically functional derivative thereof and one or more of pharmaceutically acceptable carriers, diluents and excipients.

In a six aspect, the present invention relates to a method of treating or preventing cancer or atherosclerosis; comprising administering to a mammal a therapeutically effective amount of a compound of formula I, or a salt, solvate, or a physiologically functional derivative thereof and one or more of pharmaceutically acceptable carriers, diluents and excipients.

In a seventh aspect, the present invention relates to chemical intermediates for making a compound of formula I.

In an eight aspect, the present invention relates to processes for making a compound of formula I.

DETAILED DESCRIPTION

The following terms may appear in the specification. If they appear, the following definitions will apply.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "alkyl" refers to a straight or branched chain hydrocarbons. Thus, "$C_{1-6}$ alkyl" refers to an alkyl group which contains at least 1 and at most 6 carbon atoms. Examples of "$C_{1-6}$ alkyl" groups useful in the present invention include, but are not limited to, methyl, ethyl, propyl, isopropyl, isobutyl, n-butyl, n-pentyl, n-hexyl, and the like.

As used herein, the term "alkylene" refers to a straight or branched chain divalent hydrocarbon radical. Thus, "$C_{1-6}$ alkylene" refers to an alkylene group which contains at least 1 and at most 6 carbon atoms. Examples of "$C_{1-6}$ alkylene" as used herein include, but are not limited to, methylene, ethylene, n-propylene, n-butylene, and the like.

As used herein $C_{1-6}$ cycloalkyl refers to cyclopropyl, cyclobutyl, cyclopentyl, or cyclohexyl.

Chemical notation in which a line is drawn from a center of an aromatic ring means the aromatic ring is connected from any of the possible carbon atom in the aromatic ring.

"Aryl" means phenyl or naphtyl which is optionally and independently substituted with up to three halogens and trifluoromethyl groups. For the sake of clarification, for example, aryl includes groups such as 4-chlorophenyl group, 3-trifluoromethylphenyl group, 2-fluoro-5-trifluoromethylphenyl group, and the like. And "aryloxy" includes groups such as 4-chlorophenyloxy group, 3-trifluoromethyloxy group, 2-fluoro-5-trifluoromethylphenyloxy group, and the like.

As used herein "araklyl" means an aryl group linked to $C_{1-6}$ alkylene radicals.

As used herein, the term "halogen" refers to fluorine (F), chlorine (Cl), bromine (Br), or Iodine (I).

As used herein, the term "optionally" means that the subsequently described event(s) may or may not occur, and includes both event(s), which occur, and events that do not occur.

As used herein, the term "physiologically functional derivative" refers to any pharmaceutically acceptable derivative of a compound of the present invention, for example, an ester or an amide, which upon administration to a mammal is capable of providing (directly or indirectly) a compound of the present invention or an active metabolite thereof. Such derivatives are clear to those skilled in the art, without undue experimentation, and with reference to the teaching of Burger's Medicinal Chemistry And Drug Discovery, 5th Edition, Vol 1: Principles and Practice, which is Incorporated herein by reference to the extent that it teaches physiologically functional derivatives.

As used herein, the term "solvate" refers to a complex of variable stoichiometry formed by a solute (in this invention, a compound of formula I or a salt or physiologically functional derivative thereof) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water.

As used herein, the term "substituted" refers to substitution with the named substituent or substituents, multiple degrees of substitution being allowed unless otherwise stated.

Certain of the compounds described herein may contain one or more chiral atoms, or may otherwise be capable of existing as two enantiomers. Accordingly, the compounds of this invention include mixtures of enantiomers as well as purified enantiomers or enantiomerically enriched mixtures. Also included within the scope of the invention are the individual isomers of the compounds represented by formula I above as well as any wholly or partially equilibrated mixtures thereof. The present invention also covers the individual isomers of the compounds represented by the formulas above as mixtures with isomers thereof in which one or more chiral centers are inverted. Also, it is understood that all tautomers and mixtures of tautomers are included within the scope of the compounds of formula I.

Typically, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts derived from a nitrogen on a substituent in the compound of formula I. Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium and valerate. Other salts, which are not pharmaceutically acceptable, may be useful in the preparation of compounds of this invention and these form a further aspect of the invention.

While it is possible that, for use in therapy, therapeutically effective amounts of a compound of formula I, as well as salts, solvates and physiological functional derivatives thereof, may be administered as the raw chemical, it is possible to present the active ingredient as a pharmaceutical composition. Accordingly, the invention further provides pharmaceutical compositions, which include therapeutically effective amounts of compounds of the formula I and salts, solvates and physiological functional derivatives thereof, and one or more pharmaceutically acceptable carriers, diluents, or excipients. The compounds of the formula I and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula I, or salts, solvates and physiological functional derivatives thereof, with one or more pharmaceutically acceptable carriers, diluents or excipients.

Pharmaceutical formulations may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the formula I, depending on the condition being treated, the route of administration and the age, weight and condition of the patient, or pharmaceutical formulations may be presented in unit dose forms containing a predetermined amount of active ingredient per unit dose. Preferred unit dosage formulations are those containing a daily dose or sub-dose, as herein above recited, or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of formula I, and salts, solvates and physiological functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of formula I, and salts, solvates and physiological functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active Ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the formulations may include other agents conventional in the art having regard to the type of formulation in question, for example those suitable for oral administration may include flavouring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of formula I for the treatment or prevention of a condition of inappropriate vasculogenesis, angiogenesis, vessel maturation or cell mobility caused by one or more tyrosine kinases selected from Tie-2, VEGFR-2, Src-c, or EphB4 imbalance or inappropriate activity including, but not limited to, cancer or atherosclerosis will generally be in the range of 0.1 to 100 mg/kg body weight of recipient (mammal) per day and more usually in the range of 1 to 10 mg/kg body weight per day. Thus, for a 70 kg adult mammal, the actual amount per day would usually be from 70 to 700 mg and this amount may be given in a single dose per day or more usually in a number (such as two, three, four, five or six) of sub-doses per day such that the total daily dose is the same. An effective amount of a salt or solvate, or physiologically functional derivative thereof, may be determined as a proportion of the effective amount of the compound of formula I per se. It is envisaged that similar dosages would be appropriate for treatment of the other conditions.

Method of Preparation

Compounds of general formula I may be prepared by methods known in the art of organic synthesis as set forth in part by the following synthesis schemes, or variants thereof. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) Protecting Groups in Organic Synthesis, John Wiley & Sons). These groups are removed at a convenient stage of the compound synthesis using methods that are readily apparent to those skilled in the art. The selection of processes as well as the reaction conditions and order of their execution shall be consistent with the preparation of compounds of formula I. Those skilled in the art will recognize if a stereocenter exists in compounds of formula I. Accordingly, the present invention includes both possible stereoisomers and includes not only racemic compounds but the individual enantiomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, Stereochemistry of Organic Compounds by E. L. Eliel, S. H. Wilen, and L. N. Mander (Wiley-Interscience, 1994).

More particularly, the compounds of the formula I may be made by a process depicted in Schemes A, B or B', or a variant thereof. Any person skilled in the art can readily adapt the processes of Schemes A, B to B', such the stoichemistry of the reagents, temperature, solvents, etc. to optimize the yield of the products desired.

For example, in making a compound of formula I in which Y is oxygen, Scheme A can be followed. Briefly, 2-furfural (1) is converted under heating into 3-furan-2-yl-acrylic acid (2) using malonic acid and a suitable base such as piperidine. 3-(Furan-2-yl)-acrylic acid (2) is converted into 3-(furan-2-yl)-acryloyl azide (3) using DPPA and a suitable base such as triethylamine. The azide (3) was cyclized to afford 5H-furo[3,2-c]pyridin-4-one (4) upon heating and a catalytic amount of iodine. 5H-furo[3,2-c]pyridin-4-one is chlorinated on the 4$^{th}$ position with POCl$_3$ to afford 4-chloro-furo[3,2-c]pyridine (5). 4-Chloro-furo[3,2-c]pyridine is treated with bromine, and subsequently with DBU to afford compound (6). The chlorine atom of compound (6) is replaced with an amino group by the action of aqueous ammonia to afford compound (7). Compound (7) is subsequently subjected to Pd(PPh$_3$)$_4$, sodium carbonate, R—B(OH)$_2$ or a compound of formula R—B(OR')$_2$, in which the radical —B(OR')$_2$ can be represented as

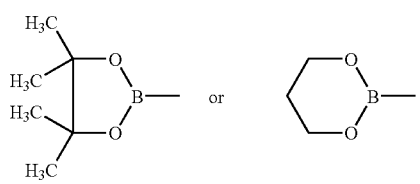

(Suzuki coupling reaction), to afford a compound of formula I'. A compound of formula I' is further brominated with N-bromosuccinimide (NBS) to afford a compound of formula I''. Further Suzuki coupling reaction on a compound of formula I'' using Pd(PPh$_3$)$_4$, sodium carbonate, R2-B(OH)$_2$ or a compound of formula R2-B(OR')$_2$, in which the radical —B(OR')$_2$ can be represented as

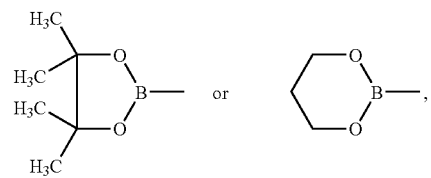

yields a compound of I'''. In Scheme A, R2 is as defined in formula I, and R is R1 or a functionality which can be converted into R1.

When a compound of formula I in which Y is S is desired, Scheme A process can be modified to obtain the desired product. Two such modifications are shown in Scheme B and B'. Processes depicted in Schemes B and B' are minor variations of Scheme A, and actual examples using the processes appear below. In Schemes B and B', R1 and R2 are as defined in formula I. As before the radical —B(OR')$_2$ in R1-B(OR')$_2$ or R2-B(OR')$_2$ can be

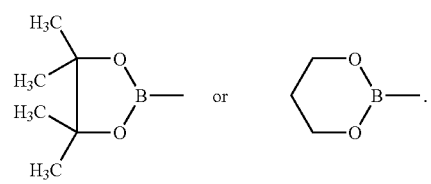

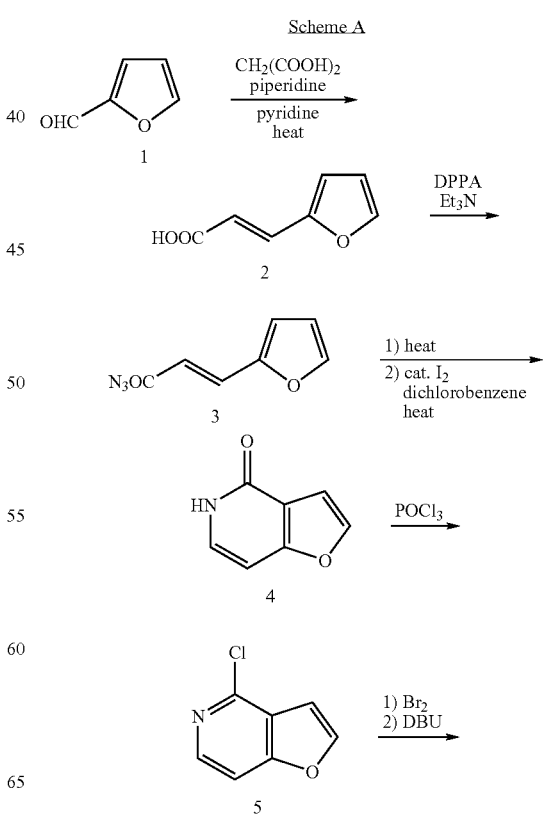

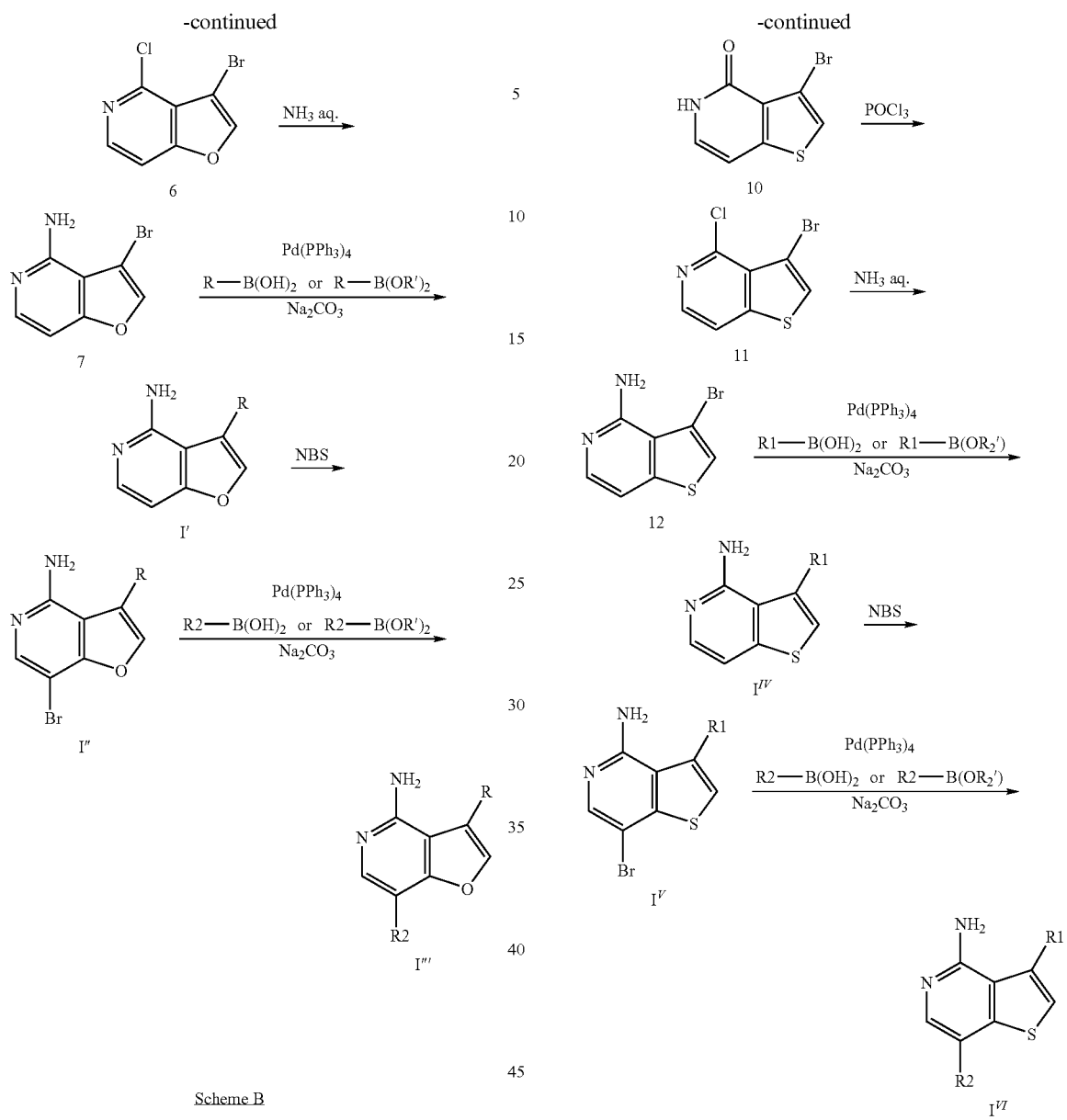
Scheme B
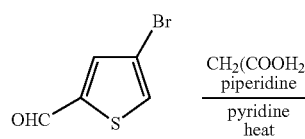
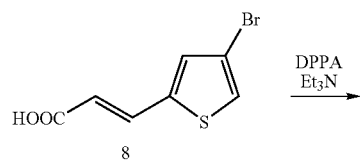
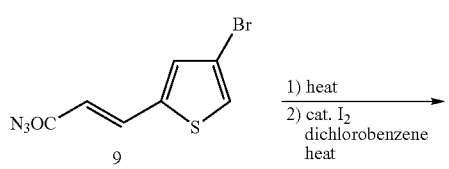
Scheme B'
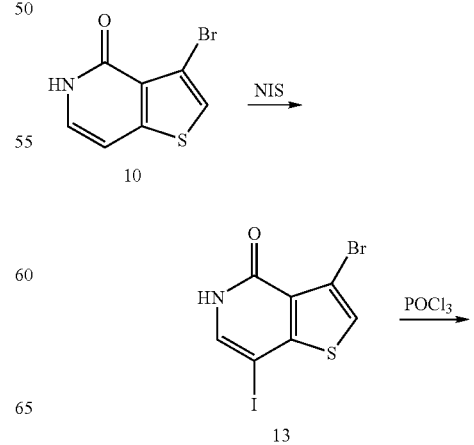

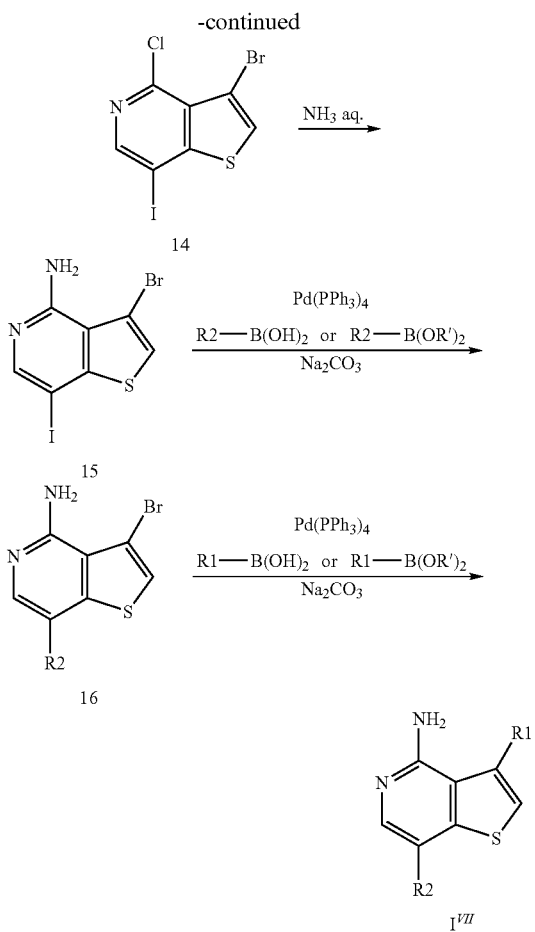

SPECIFIC EMBODIMENTS

Examples

As used herein the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

g (grams);
L (liters);
μL (microliters);
M (molar);
i. v. (intravenous);
MHz (megahertz);
mmol (millimoles);
min (minutes);
mp (melting point);
Tr (retention time);
MeOH (methanol);
TEA (triethylamine);
TFAA (trifluoroacetic anhydride);
DMSO (dimethylsulfoxide);
DME (1,2-dimethoxyethane);
DCE (dichloroethane);
DMPU (N,N'-dimethylpropyleneurea);
IBCF (isobutyl chloroformate);
HOSu (N-hydroxysuccinimide);
mCPBA (meta-chloroperbenzoic acid;
BOC (tert-butyloxycarbonyl);
DCC (dicyclohexylcarbodiimide);
Ac (acetyl);
TMSE (2-(trimethylsilyl)ethyl);
TIPS (triisopropylsilyl);
DMAP (4-dimethylaminopyridine);
ATP (adenosine triphosphate);
DMEM (Dulbecco's modified Eagle medium);
mg (milligrams);
mL (milliliters);
psi (pounds per square inch);
mM (millimolar);
Hz (Hertz);
mol (moles);
rt (room temperature);
h (hours);
TLC (thin layer chromatography);
RP (reverse phase);
i-PrOH (isopropanol);
TFA (trifluoroacetic acid);
THF (tetrahydrofuran);
AcOEt (ethyl acetate);
DCM (dichloromethane);
DMF (N,N-dimethylformamide);
(CDI (1,1-carbonyldiimidazole);
HOAc (acetic acid);
HOBT (1-hydroxybenzotriazole);
EDC (ethylcarbodiimide hydrochloride);
FMOC (9-fluorenylmethoxycarbonyl);
CBZ (benzyloxycarbonyl);
atm (atmosphere);
TMS (trimethylsilyl);
TBS (t-butyldimethylsilyl);
BSA (bovine serum albumin)
HRP (horseradish peroxidase);
HPLC (high pressure liquid chromatography);
BOP (bis(2-oxo-3-oxazolidinyl)phosphinic chloride);
TBAF (tetra-n-butylammonium fluoride);
HBTU (O-Benzotriazole-1-yl-N,N,N',N'-tetramethyluronium hexafluorophosphate).
HEPES (4-(2-hydroxyethyl)-1-piperazine ethane sulfonic acid);
DPPA (diphenylphosphoryl azide);
fHNO3 (fumed HNO3); and
EDTA (ethylenediaminetetraacetic acid).

All references to ether are to diethyl ether; brine refers to a saturated aqueous solution of NaCl. Unless otherwise indicated, all temperatures are expressed in ° C. (degrees Centigrade). All reactions are conducted under an inert atmosphere at room temperature unless otherwise noted.

$^1$H NMR spectra were recorded on a Brucker AVANCE-400. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet), br (broad).

LC-MS were recorded on a micromass ZMD and Waters 2690. All mass spectra were taken under electrospray ionization (ESI) methods. Most of the reactions were monitored by

Example 1

4-Amino-3-(4-((2-fluoro-5-(trifluoromethyl)aminocarbonylamino)phenyl)-7-(3-chlorophenyl)-furo[3,2-c]pyridine (Ia)

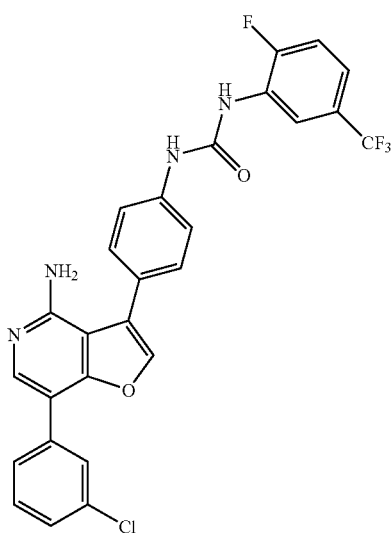

a) 3-(Furan-2-yl)-acrylic acid (2)

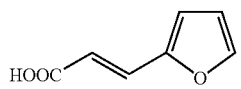

The mixture of 2-furfural (15 g, 0.15 mol), malonic acid (17.9 g, 0.17 mol) and piperidine(1.5 ml, 0.016 mol) in 80 ml of pyridine was stirred for 5 hours at 100° C. and then refluxed for 20 min, which was cooled down to room temperature and poured into water (180 ml), and resultant mixture was acidified with concentrated HCl. The generated precipitate was collected by filtration and dried under the reduced pressure to give 3-(furan-2-yl)-acrylic acid (16.8 g). 1H NMR (400 MHz, DMSO-$d_6$) ppm 12.44 (brs, 1H), 7.83 (d, J=1.8 Hz, 1H), 7.40 (d, J=15.9 Hz, 1H), 6.93 (d, J=3.3 Hz, 1H), 6.63 (dd, J=1.8, 3.3 Hz, 1H), 6.17 (d, J=15.7 Hz, 1H).

b) 3-(Furan-2-yl)-acryloyl azide (3)

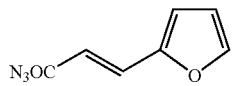

To the solution of 3-(furan-2-yl)-acrylic acid (15.7 g, 0.11 mol) and Et$_3$N (19 ml, 0.14 mol) THF (300 ml) was added DPPA (27 ml, 0.13 mmol) at 0° C. and stirred for 4 hours at room temperature; the solution was poured into the mixture of ethyl acetate and saturated NaHCO$_3$. The organic phase was separated, dried over Na$_2$SO$_4$ and then concentrated. During evaporation, precipitate was generated, which was collected and washed with MeOH, and dried under the reduced pressure to give 3-(furan-2-yl)-acryloyl azide (12.6 g). 1H NMR (400 MHz, DMSO-$d_6$) ppm 7.93 (d, J=1.5 Hz, 1H), 7.59 (d, J=15.7 Hz, 1H), 7.12 (d, J=3.3 Hz, 1H), 6.70 (dd, J=1.9, 3.4 Hz, 1H), 6.25 (d, J=15.7 Hz, 1H).

c) 5H-Furo[3,2-c]pyridin-4-one (4)

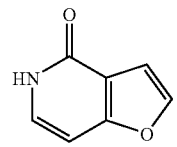

3-(Furan-2-yl)-acryloyl azide (12.6 g) was dissolved in 100 ml of toluene and the resultant solution was heated up to 120° C. and stirred for 30 min. After evaporation of solvent, o-dichlorobenzene (100 ml) and a few flakes of iodine were added and resultant reaction mixture was heated up to 170° C. and stirred for 2 hours. The mixture was cooled down to ambient temperature and to this was added Et$_2$O (100 ml). The undissolved matter was filtered off and the filtrate was poured into a mixture of Et$_2$O (100 ml), 1N NaOH (100 ml) and water (100 ml). The corresponding aqueous layer was collected, which was acidified by 2N HCl and extracted with ethyl acetate. The organic layer was separated and dried over Na$_2$SO$_4$, filtered and concentrated in vacuo. The residue was precipitated from Et$_2$O, which was collected and dried under the reduced pressure to give 5H-furo[3,2-c]pyridin-4-one (6.7 g) 1H NMR (400 MHz, DMSO-$d_6$) ppm 11.44 (brs, 1H), 7.87 (d, J=2.3 Hz, 1H), 7.29 (d, J=7.1 Hz, 1H), 6.93 (dd, J=2.1, 0.9 Hz, 1H), 6.66 (dd, J=0.8, 7.1 Hz, 1H).

d) 4-Chloro-furo[3,2-c]pyridine (5)

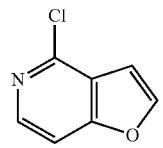

5H-Furo[3,2-c]pyridin-4-one (5.9 g) was suspended with POCl$_3$ (12 ml) and the reaction mixture was stirred for 3 hours at 120° C. After evaporating POCl$_3$, crushed ice was added and poured into the mixture of ethyl acetate and saturated NaHCO$_3$. The corresponding organic phase was separated and dried over Na$_2$SO$_4$ and then concentrated in vacuo. The resultant residue was purified by chromatography on a silica gel column to afford 4-chloro-furo[3,2-c]pyridine (5.6 g) 1H NMR (400 MHz, DMSO-$d_6$) ppm 8.31 (d, J=5.8 Hz, 1H), 8.26 (d, J=2.3 Hz, 1H), 7.79 (dd, J=1.0, 5.6 Hz, 1H), 7.13 (dd, J=1.0, 2.3 Hz, 1H).

e) 4-Chloro-3-bromo-furo[3,2-c]pyridine (6)

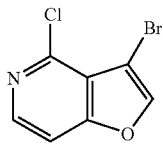

To the solution of 4-chloro-furo[3,2-c]pyridine (4.2 g, 0.03 mol) In CCl$_4$ (77 ml) was added Br$_2$ (2.4 ml, 0.046 mol) at 0° C. and the resultant reaction mixture was stirred for 4 hours at room temperature. The resultant suspension was poured into the mixture of ethyl acetate and 10% Na$_2$SO$_3$. The corresponding organic phase was separated and dried over Na$_2$SO$_4$ and concentrated in vacuo. The crude residue was dissolved in THF (100 ml) and DBU (1,8-diazabicyclo[5.4.0]undec-7-ene) (5.6 ml) was added at 0° C. The resultant reaction mixture was stirred for 2 hours at room temperature and poured into NaHCO$_3$ and ethyl acetate. The organic layers were separated, dried over anhydrous sodium sulfate, filtered and concentrated to dryness. The residue was purified by chromatography on a silica gel column to afford the titled compound (5.4 g) 1H NMR (400 MHz, CDCl$_3$) ppm 8.32 (d, J=5.8 Hz, 1H), 7.72 (s, 1H), 7.44 (d, J=5.8 Hz, 1H), 7.26 (s, 1H).

f) 4-Amino-3-bromo-furo[3,2-c]pyridine (7)

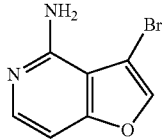

To the solution of 3-bromo-4-chloro-furo[3,2-c]pyridine (3.0 g) in 40 ml of dioxane was added 28% ammonia solution (15 ml) in an autoclave and put into the oil bath. The reaction mixture was allowed to heat up to 150° C. and stir for 5 days at 150° C. The resultant mixture was poured into ethyl acetate and brine. The organic phases was separated, dried over anhydrous sodium sulfate, filtered and concentrated in vacuo. The residue was purified by chromatography on a silica gel column to afford 3-bromo-furo[3,2-c]pyridin-4-ylamine (1.3 g). 1H NMR (400 MHz, CDCl3) ppm 7.93 (d, J=6.1 Hz, 1H), 7.52 (s, 1H), 6.87 (d, J=5.8 Hz, 1H). MS: m/z 213, 215 (M+H)$^+$.

g) 4-Amino-3-(4-aminophenyl)-furo[3,2-c]pyridine (I'a)

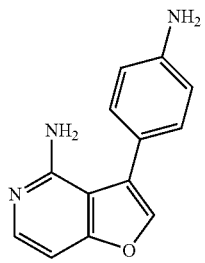

The mixture of 4-amino-3-bromo-furo[3,2-c]pyridine (7) (63 mg, 0.29 mmol), 4-(4,4,5,5-tetramethyl-1,3,2-dioxaborolan-2-yl)aniline (84 mg, 0.38 mmol), Pd(PPh$_3$)$_4$ (34 mg, 0.029 mmol) and sodium carbonate (0.74 ml, 1.5 mmol) in 3 ml of DME was stirred for 14 hours at 80° C. The solvent was removed, and the resultant residue was purified by chromatography on a silica gel column gel to afford the titled compound (55 mg) 1H NMR (400 MHz, DMSO-d$_6$) ppm 7.82 (d, J=6.1 Hz, 1H), 7.77 (s, 1H), 7.15 (d, J=8.3 Hz, 2H), 6.89 (d, J=5.8 Hz, 1H), 6.69 (d, J=8.3 Hz, 2H), 5.49 (s, 2H), 5.32 (s, 2H). MS: m/z 226 (M+H)$^+$.

h) 4-Amino-3-(4-((2-fluoro-5-(trifluoromethyl)aminocarbonylamino)phenyl)-furo[3,2-c]pyridine (Ib)

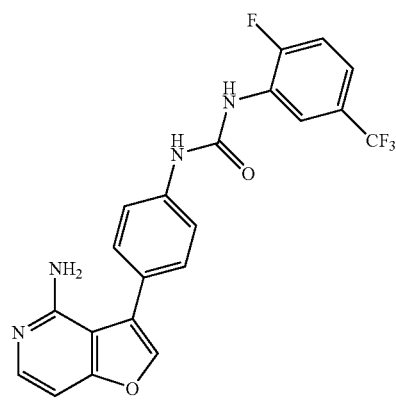

To the solution of 4-amino-3-(4-aminophenyl)-furo[3,2-c]pyridine (36 mg, 0.16 mmol) in 2 ml of THF was added 2-fluoro-5-trifluoromethyl-phenylisocyanate (25 ul, 0.17 mmol) and stirred for 2 hours at 0° C. The mixture was then evaporated and the crude product was purified by chromatography on a silica gel column to afford the titled compound as a solid (35 mg). 1H NMR (400 MHz, DMSO-d$_6$) ppm 9.46 (s, 1H), 9.07 (s, 1H), 8.70 (d, J=7.3, 2.0 Hz, 1H), 8.00 (s, 1H), 7.93 (d, J=5.8 Hz, 1H), 7.69 (d, J=8.6 Hz, 2H), 7.53 (d, J=8.3 Hz, 2H), 7.60-7.56 (m, 1H), 7.49-7.45 (m, 1H), 5.60 (s, 2H). MS: m/z 431 (M+H)$^+$.

I) 4-Amino-3-(4((2-fluoro-5-(trifluoromethyl)aminocarbonylamino)phenyl)-7-bromo-furo[3,2-c]pyridine (Ic)

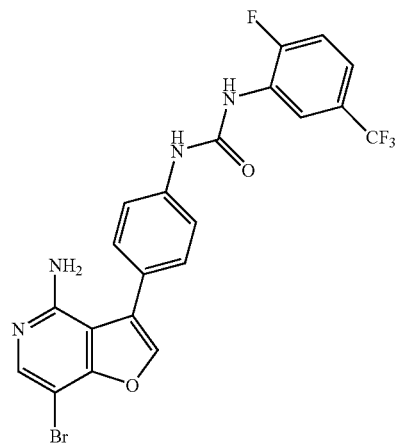

To the solution of 4-amino-3-(4-((2-fluoro-5-(trifluoromethyl)aminocarbonyl amino)phenyl)-furo[3,2-c]pyridine (710 mg, 1.65 mmol) in THF cooled at −78° C. was added NBS (294 mg, 1.65 mmol) and the reaction mixture was allowed to warm up to 0° C. over a period of 2 hours. The resultant mixture was poured into 10% $Na_2SO_3$ and ethyl acetate, the organic phase was collected, dried over $Na_2SO_4$, filtered and concentrated in vacuo. The residue was purified by chromatography on a silica gel column to afford the titled compound (347 mg) 1H NMR (400 MHz, DMSO-$d_6$) ppm 9.41 (s, 1H), 9.01 (s, 1H), 8.64 (dd, J=2.3, 7.3 Hz, 1H), 8.09 (s, 1H), 7.98 (s, 1H), 7.64 (d, J=8.6 Hz, 2H), 7.54-7.50 (m, 1H), 7.48 (d, J=8.6 Hz, 2H), 7.44-7.40 (m, 1H), 5.75 (s, 2H). MS: m/z 509, 511 $(M+H)^+$.

j) 4-Amino-3(4-((2-fluoro-5-(trifluoromethyl)aminocarbonylamino)phenyl)-7-(3-chlorophenyl)furo[3,2-c]pyridine (Ia)

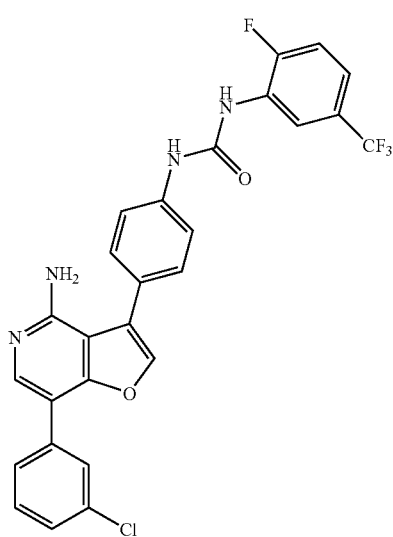

The mixture of 4-amino-3-(4-((2-fluoro-5-(trifluoromethyl)aminocarbonylamino) phenyl)-7-bromo-furo[3,2-c]pyridine (30 mg, 0.059 mmol), Pd(PPh$_3$)$_4$ (10 mg, 10 mol %), 3-chlorophenylboronic acid (13.8 mg, 0.089 mmol) and 2M $Na_2CO_3$ aqueous solution (0.15 ml, 0.30 mmol) in DME (4 ml) was stirred for 14 hours at 80° C. As starting material remained, same amount of reagents described above and DMF (2 ml) were added and stirred for 5 hours at 100° C. The resultant mixture was directly applied to SCX (Varian, 5 g) and the eluted with 1N $NH_3$ in $CHCl_3$ and MeOH and the elutant concentrated in vacuo. The residue was purified by chromatography on a silica gel column to afford the titled compound (9.8 mg). 1H NMR (400 MHz, DMSO-$d_6$) ppm 9.44 (s, 1H), 9.04 (s, 1H), 8.64 (dd, J=2.0, 7.1 Hz, 1H), 8.20 (s, 1H), 8.08 (s, 1H), 7.88 (dd, J=1.9 Hz, 1H), 7.80 (d, J=7.8 Hz, 1H), 7.65 (d, J=8.6 Hz, 2H), 7.54-7.49 (m, 4H), 7.43-7.41 (m, 2H), 5.78 (m, 1H).

MS: m/z 541, 543 $(M+H)^+$.

Example 2

4-Amino-3-(4-((2-fluoro-5-(trifluoromethyl)aminocarbonylamino) phenyl)-7-(3-sulfamoylphenyl)-furo[3,2-c]pyridine (Id)

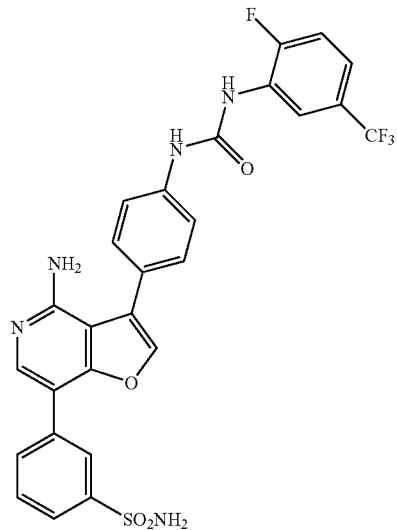

In a similar manner as described in Example 1j, the title compound was obtained from compound Ic and 3-(4,4,5,5-tetramethyl-[1,3,2]dioxaborolan-2-yl)-benzenesulfonamide as a solid. 1H NMR (400 MHz, DMSO-$d_6$) ppm 9.51 (s, 1H), 9.09 (s, 1H), 8.63 (dd, J=2.1, 7.2 Hz, 1H), 8.29 (dd, J=1.6 Hz, 1H), 8.20 (s, 1H), 8.09 (s, 1H), 8.03 (d, J=8.1 Hz, 1H), 7.80 (d, J=7.8 Hz, 1H), 7.71-7.65 (m, 3H), 7.52-7.50 (m, 3H), 7.43-7.39 (m, 3H), 5.80 (s, 2H), MS: m/z 586 $(M+H)^+$.

Example 3

4-Amino-3-(4-((2-fluoro-5-(trifluoromethyl)aminocarbonylamino)phenyl)-7-(3-pyridyl)-furo[3,2-c]pyridine (Ie)

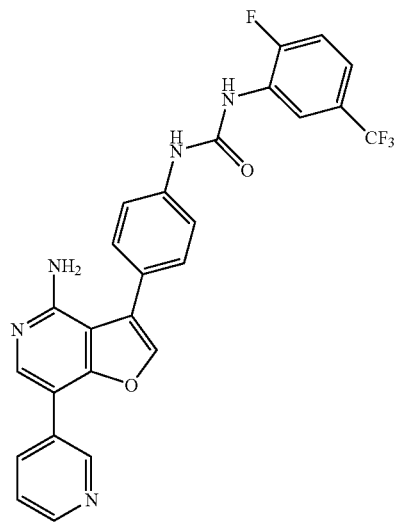

In a similar manner as described in Example 1j, the title compound was obtained from compound Ic and pyridine-3-boronic acid 1,3-propanediol cyclic ester as a solid. 1H NMR (400 MHz, DMSO-d$_6$) ppm 9.46 (s, 1H), 9.06 (s, 1H), 9.02 (d, J=2.3 Hz, 1H), 8.63 (dd, J=2.1, 7.2 Hz, 1H), 8.56 (dd, J=1.5, 4.8 Hz, 1H), 8.21-8.19 (m, 2H), 8.07 (s, 1H), 7.66 (d, J=8.6 Hz, 2H), 7.54-7.49 (m, 4H), 7.43-7.39 (m, 1H), 5.79 (s, 2H). MS: m/z 508 (M+H)$^+$.

Example 4

4-Amino-3-(3-chloro-4-fluoro-phenyl)-7-(3-sulfamoylphenyl)-thieno[3,2-c]pyridine (If)

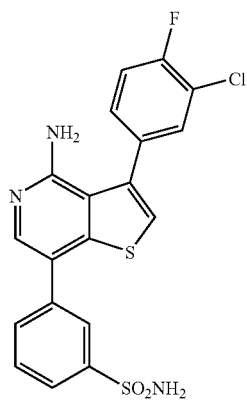

The title compound was prepared from 4-bromo-thiophene-2-carbaldehyde according to similar procedure for the preparation of Example 1 as shown in Scheme B.

a) 3-(4-Bromo-thiophen-2-yl)-acrylic acid (8)

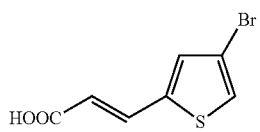

The mixture of 4-bromo-thiophene-2-carbaldehyde (10 g, 0.052 mol), malonic acid (6.5 g, 0.063 mol) and piperidine (0.5 ml) in pyridine (40 ml) was stirred for 14 hours at 100° C., which was cooled down to room temperature and poured into water, and resultant mixture was acidified with concentrated HCl. The generated precipitate was collected by filtration, which was suspended with EtOH (50 ml) and water (100 ml). The precipitate was collected by filtration and dried under the reduced pressure to give 3-(4-bromo-thiophen-2-yl)-acrylic acid (14 g). 1H NMR (400 MHz, DMSO-d$_6$) ppm 7.79 (s, 1H), 7.67 (d, J=15.9 Hz, 1H), 7.56 (s, 1H), 6.26 (d, J=15.9 Hz, 1H).

b) 3-(4-Bromo-thiophen-2-yl)-acryloyl azide (9)

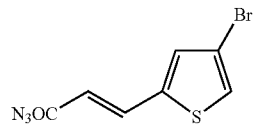

To the solution of 3-(4-bromo-thiophen-2-yl)-acrylic acid (14.0 g, 0.06 mol) and Et$_3$N (10 ml, 0.07 mol) in THF (150 ml) was added DPPA (14 ml, 0.066 mmol) at 0° C. and stirred for 4 hours at room temperature, poured into the mixture of ethyl acetate and saturated NaHCO$_3$. The organic phase was separated, dried over Na$_2$SO$_4$ and then concentrated. During evaporation, precipitate was generated, which was suspended with MeOH (75 ml) and water (75 ml). The precipitate was collected, washed with water and dried under the reduced pressure to give 3-(4-bromo-thiophen-2-yl)-acryloyl azide (11.6 g). 1H NMR (400 MHz, DMSO-d$_6$) ppm 7.95 (s, 1H), 7.87 (d, J=15.4 Hz, 1H), 7.75 (s, 1H), 6.44 (d, J=15.7 Hz, 1H).

c) 3-Bromo-5H-thieno[3,2-c]pyridin-4-one (10)

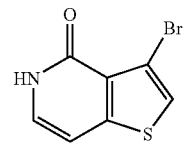

3-(4-Bromo-thiophen-2-yl)-acryloyl azide (6.0 g) was dissolved in toluene (100 ml) and the resultant solution was heated up to 120° C. and stirred for 30 min. After evaporation of solvent, 100 ml of o-dichlorobenzene and a few flakes of iodine were added and resultant reaction mixture was heated up to 170° C. and stirred for 2 hours. The mixture was cooled down to ambient temperature. The generated precipitate was collected by filtration, washed with EtOH and dried under the reduced pressure to afford 3-bromo-5H-thieno[3,2-c]pyridin-4-one (2.6 g). 1H NMR (400 MHz, DMSO-d$_6$) ppm 11:49 (s, 1H), 7.68 (s, 1H), 7.28 (dd, J=6.3 Hz, 1H), 6.87 (d, J=7.1 Hz, 1H).

d) 3-Bromo-4-chloro-thieno[3,2-c]pyridine (11)

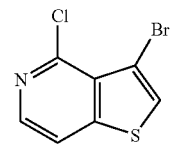

3-Bromo-5H-thieno[3,2-c]pyridin-4-one (1.0 g) and POCl$_3$ (3 ml) was stirred for 1.5 hours at 120° C. After evaporation of POCl$_3$, crushed ice was added to the residue and generated precipitate was collected by filtration to afford 3-bromo-4-chloro-thieno[3,2-c]pyridine (1.1 g) 1H NMR (400 MHz, DMSO-d$_6$) ppm 8.31 (d, J=5.6 Hz, 1H), 5.27-8.21 (m, 2H).

e) 4-Amino-3-bromo-thieno[3,2-c]pyridine (12)

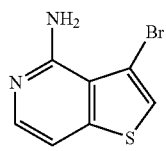

To the solution of 3-bromo-4-chloro-thieno[3,2-c]pyridine (3.2 g) in dioxane (30 ml) was added 28% ammonia solution (10 ml) in an autoclave and put into the oil bath. The reaction mixture was allowed to heat up to 150° C. and stir for 4 days at 150° C. The resultant mixture was concentrated in vacuo and the residue was purified by chromatography on a silica gel column to afford 3-bromo-thieno[3,2-c]pyridin-4-ylamine (1.7 g) 1H NMR (400 MHz, DMSO-d$_6$) ppm 7.84 (d, J=5.6 Hz, 1H), 7.78 (s, 1H), 7.27 (d, J=5.6 Hz, 1H), 6.51 (s, 2H). MS: m/z 229, 231 (M+H)$^+$.

f) 4-Amino-3-(3-chloro-4-fluoro-phenyl)thieno[3,2-c]pyridine (Ig)

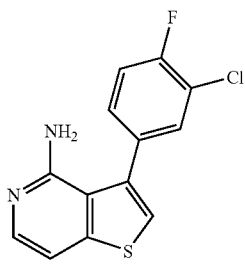

The mixture of 4-amino-3-bromo-thieno[3,2-c]pyridine (12) (300 mg 1.24 mmol), 3-chloro-4-fluoro-benzenboronic acid (432 mg, 2.48 mmol), Pd(PPh$_3$)$_4$ (215 mg, 10 mol %) and sodium carbonate (3.1 ml, 6.0 mmol) in 30 ml of DME was stirred for 14 hours at 80° C. The resultant mixture was directly applied to SCX (benzenesulphonicacid-based strong cation exchange sorbent:Varian, 10 g) and eluted with 1N NH$_3$ in CHCl$_3$ and MeOH. The eluant was collected and concentrated in vacuo. The residue was purified by chromatography on a silica gel column to afford the title compound (295 mg). 1H NMR (400 MHz, DMSO-d$_6$) ppm 7.58 (d, J=5.6 Hz, 1H), 7.71 (dd, J=2.1, 7.2 Hz, 1H), 7.57 (s, 1H), 7.54 (dd, J=9.1 Hz, 1H), 7.47 (ddd, J=2.1, 4.8, 8.5 Hz, 1H), 7.29 (d. J=5.8 Hz, 1H), 5.42 (s, 2H). MS: m/z 279, 281 (M+H)$^+$.

q) 4-Amino-7-bromo-3-(3-chloro-4-fluoro-phenyl) thieno[3,2-c]pyridine (Ih)

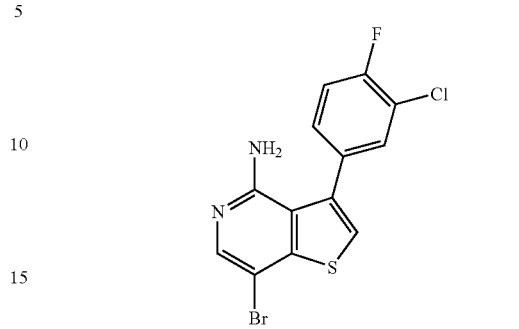

To the solution of 4-amino-3-(3-chloro-4-fluoro-phenyl) thieno[3,2-c]pyridine (240 mg, 0.86 mmol) in 10 ml of THF cooled at 0° C. was added NBS (153 mg, 0.86 mmol) and the reaction mixture was stirred for 1 hour at 0° C. The resultant mixture was poured into 10% Na$_2$SO$_3$ and ethyl acetate, the organic phase was collected, dried over Na$_2$SO$_4$, filtered and concentrated in vacuo. The residue was purified by chromatography on a silica gel column to afford the titled compound (333 mg). 1H NMR (400 MHz, DMSO-d$_6$) ppm 7.97 (s, 1H), 7.73 (dd, J=2.1, 7.2 Hz, 1H), 7.69 (s, 1H), 7.55 (dd, J=8.8 Hz, 1H), 7.48 (ddd, J=2.2, 4.7, 8.4 Hz, 1H), 5.66 (s, 2H). MS: m/z 357, 359, 361 (M+H)$^+$.

h) 4-Amino-3-(3-chloro-4-fluoro-phenyl)-7-(3-sulfamoylphenyl)thieno[3,2-c]pyridine (If)

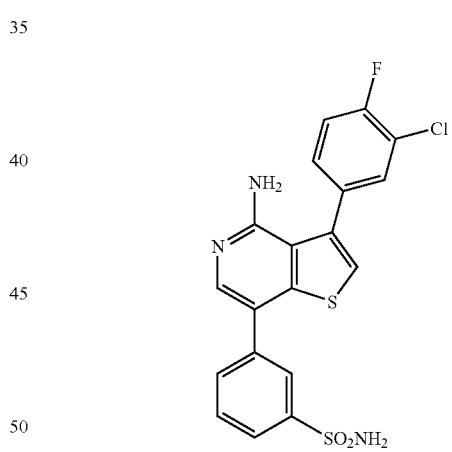

The mixture of 4-amino-7-bromo-3-(3-chloro-4-fluorophenyl)thieno[3,2-c]pyridine (40 mg, 0.112 mmol), Pd(PPh$_3$)$_4$ (19 mg, 10 mol %), 3-(4,4,5,5-tetramethyl-[1,3,2] dioxaborolan-2-yl)-benzenesulfonamide (36.8 mg, 0.224 mmol) and 2M Na$_2$CO$_3$ aqueous solution (0.28 ml, 0.56 mmol) in 2 ml of DME was stirred for 14 hours at 80° C. As starting material remained, same amount of reagents described above and DMF (2 ml) were added and stirred for 5 hours at 100° C. The resultant mixture was directly applied to SCX (Varian, 5 g) and eluted with 1N NH$_3$ in CHCl$_3$ and MeOH was collected, and the eluant was concentrated in vacuo. The residue was purified by chromatography on a silica gel column to afford the titled compound (9.8 mg) 1H NMR (400 MHz, DMSO-d$_6$) ppm 8.12 (dd, J=1.8 Hz, 1H), 8.0 s, 1H), 7.91 (ddd, J=1.5, 1.5, 7.6 Hz, 1H), 7.85 (ddd, J=1.4, 1.4, 7.1 Hz, 1H), 7.75 (dd, J=7.8 Hz, 1H), 7.67 (s, 1H), 7.57 (dd, J=9.0 Hz, 1H), 7.51 (ddd, J=2.2, 4.9, 8.5 Hz, 1H), 7.45 (s, 2H), 5.66 (s, 2H). MS: m/z 434 (M+H)+.

Example 5

4-Amino-3-(3-chloro-4-fluoro-Phenyl)-7-(3-acetamidephenyl)thieno[3,2-c]pyridine (Ij)

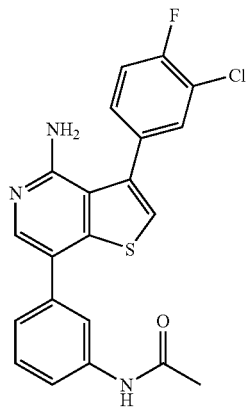

In a similar manner as described in Example 4h, the title compound was obtained from compound Ih and 3-acetamidobenzeneboronic acid as a solid. 1H NMR (400 MHz, DMSO-d$_6$) ppm 7.98 (dd, J=1.6 Hz, 1H), 7.90 (s, 1H), 7.59-7.57 (m, 1H), 7.45 (dd. J=2.1, 7.2 Hz, 1H), 7.63 (s, 1H), 7.56 (dd, J=8.8 Hz, 1H), 7.51 (ddd, J=2.1, 4.9, 8.5 Hz, 1H), 7.43 (dd, J=8.0 Hz, 1H), 7.32-7.30 (m, 1H), 5.54 (s, 2H), 2.01 (s, 3H). MS: m/z 412, 414 (M+H)+.

Example 6

4-Amino-3-(3-chloro-4-fluoro-phenyl)-7-(3-pyridyl)-thieno[3,2-c]pyridine (Ik)

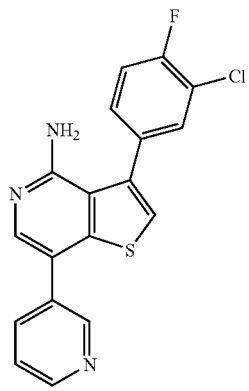

In a similar manner as described in Example 4h, the title compound was obtained from compound Ih and pyridine-3-boronic acid 1,3-propanediol cyclic ester as a solid. 1H NMR (400 MHz, DMSO-d$_6$) ppm 8.91-8.87 (m, 1H), 8.62 (dd, J=1.5, 4.8 Hz, 1H), 8.11-8.07 (m, 1H), 7.99 (s, 1H), 7.75 (dd, J=2.0, 7.1 Hz, 1H), 7.65 (s, 1H), 7.59-7.54 (m, 2H), 7.50 (ddd, J=2.2, 4.9, 8.4 Hz, 1H), 5.65 (s, 2H). MS: m/z 356, 358 (M+H)+.

Example 7

4-Amino-3-(3-chloro-4-fluoro-phenyl)-7-(3-methansulfonylphenyl)thieno-[3,2-c]pyridine (Il)

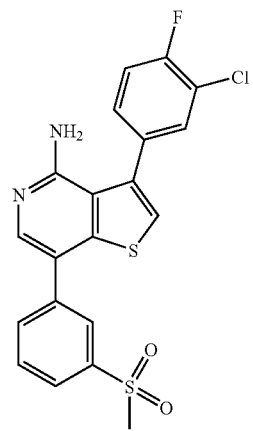

In a similar manner as described in Example 4h, the title compound was obtained from compound Ih and 3-(methanesulfonyl)phenylboronic acid as a solid. 1H NMR (400 MHz, DMSO-d$_6$) ppm 8.19 (dd, J=1.8 Hz, 1H), 8.06-8.04 (m, 2H), 7.96 (ddd, J=1.1, 1.3, 7.8 Hz, 1H), 7.81 (dd, J=7.8 Hz, 1H), 7.74 (dd, J=2.1, 7.2 Hz, 1H), 7.66 (s, 1H), 7.57 (dd, J=8.8 Hz, 1H), 7.50 (ddd, J=2.1, 4.8, 8.5 Hz, 1H), 5.69 (s, 2H), 3.31 (s, 3H). MS: m/z 433, 435 (M+H)+.

Example 8

4-Amino-3-(3-chloro-4-fluoro-phenyl)-7-(3-cyanophenyl)-thieno[3,2-c]pyridine (Im)

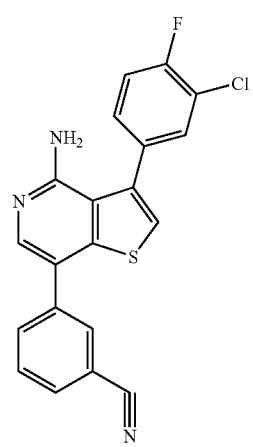

In a similar manner as described in Example 4h, the title compound was obtained from compound Ih and 3-cyanophenylboronic acid as a solid. 1H NMR (400 MHz, DMSO-d$_6$) ppm 8.23 (dd, J=1.8 Hz, 1H), 8.02 (s, 1H), 8.00-7.98 (m, 1H), 7.96-7.93 (m, 1H), 7.75 (dd, J=2.1, 7.2 Hz, 1H), 7.69 (dd, J=7.7 Hz, 1H), 7.65 (s, 1H), 7.57 (dd, J=9.0 Hz, 1H), 7.51 (ddd, J=2.1, 4.8, 8.5 Hz, 1H), 5.62 (s, 2H), 2.66 (s, 3H). MS: m/z 380, 382 (M+H)⁺.

Example 9

4-Amino-3-(3-chloro-4-fluoro-phenyl)-7-(3-acetylphenyl)-thieno[3,2-c]pyridine (In)

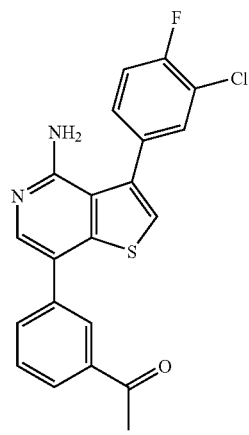

In a similar manner as described in Example 4h, the title compound was obtained from compound Ih and 3-acetylphenylboronic acid as a solid. 1H NMR (400 MHz, DMSO-d₆) ppm 8.23 (dd, J=1.8 Hz, 1H), 8.02 (s, 1H), 8.00-7.98 (m, 1H), 7.96-7.93 (m, 1H), 7.75 (d, J=2.1, 7.2 Hz, 1H), 7.69 (dd, J=7.7 Hz, 1H), 7.65 (s, 1H), 7.57 (dd, J=9.0 Hz, 1H), 7.51 (ddd, J=2.1, 4.8, 8.5 Hz, 1H), 5.62 (s, 2H), 2.66 (s, 3H). MS: m/z 397, 399 (M+H)⁺.

Example 10

4-Amino-3-(3-hydroxyphenyl)-thieno[3,2-c]pyridine (Io)

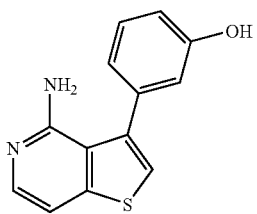

In a similar manner as described in Example 4f, the title compound was obtained from compound 12 and 3-(4,4,5,5-tetramethyl-1,3,2-dioxaborolan-2-yl)phenol as a solid. 1H NMR (400 MHz, DMSO-d₆) ppm 9.85 (s, 1H), 7.82 (d, J=5.6 Hz, 1H), 7.45 (s, 1H), 7.32 (dd, J=7.8 Hz, 1H), 7.27 (d, J=5.81 Hz, 1H), 6.90-6.80 (m, 3H), 5.51 (s, 2H). MS: m/z 243 (M+H)⁺.

Example 11

4-Amino-3-(4-chlorophenyl)-7-(3,4,5-trimethoxyphenyl)-thieno[3,2-c]pyridine (Ip)

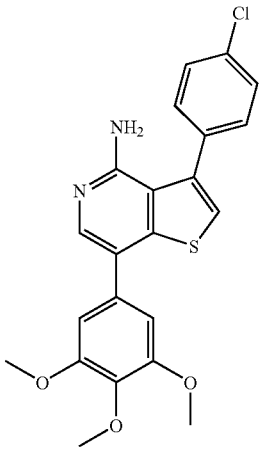

The title compound was prepared according to the procedure as shown in the scheme B'.

a) 3-Bromo-7-Iodo-5H-thieno[3,2-c]pyridin-4-one (13)

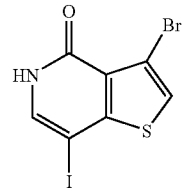

The mixture of compound 10 (see Example 4(c)) (1.9 g, 8.3 mmol) and N-iodosuccimide (NIS, 2.2 g, 49.9 mmol) in DMF (25 ml) and THF (20 ml) was stirred for 5 hours at 40° C. The reaction mixture was poured into 10% Na₂SO₃ and ethyl acetate. The insoluble product was collected by filtration, washed with ethyl acetate and dried under reduced pressure to give 3-bromo-7-iodo-5H-thieno[3,2-c]pyridin-4-one (990 mg). The filtrate was collected, dried over Na₂SO₄, filtered and concentrated in vacuo. The generated precipitate was washed with MeOH to further yield 3-bromo-7-iodo-5H-thieno[3,2-c]pyridin-4-one (1.1 g). 1H NMR (400 MHz, DMSO-d₆) ppm 11.75 (s, 1H), 7.79 (s, 1H), 7.57 (s, 1H).

b) 3-Bromo-4-chloro-7-iodo-[3,2-c]pyridine (14)

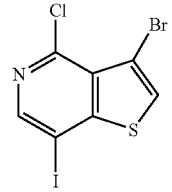

The mixture of 3-bromo-7-iodo-5H-thieno[3,2-c]pyridin-4-one (2.3 g, 6.46 mmol), dimethylaniline (1.6 ml, 12.9 mmol) and POCl₃ (6.3 ml, 67.6 mmol) was stirred for 3 hours at 120° C. After evaporation of the solvent, to the residue was added crushed ice and the generated precipitate was collected, washed with water and dried under the reduced pressure to yield 3-bromo-4-chloro-7-iodo-[3,2-c]pyridine (2.4 g). 1H NMR (400 MHz, DMSO-d$_6$) ppm 8.59 (s, 1H), 8.33 (s, 1H).

c) 4-Amino-3-bromo-7-iodo-thieno[3,2-c]pyridine (15)

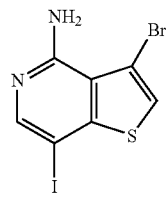

The mixture of 3-bromo-4-chloro-7-Iodo-[3,2-c]pyridine (2.1 g, 5.6 mmol) and 28% ammonia solution (10 ml) in dioxane (20 ml) in an autoclave was stirred for 7 days at 150° C. After cooling to ambient temperature the insoluble product was collected and washed with Et$_2$O and dried under the reduced pressure to afford 4-amino-3-bromo-7-iodo-[3,2-c]pyridine (800 mg). The filtrate was concentrated in vacuo and the generated precipitate was collected, washed with methanol and dried under the reduced pressure to give 4-amino-3-bromo-7-iodo-[3,2-c]pyridine (1.0 g) 1H NMR (400 MHz, DMSO-d$_6$) ppm 8.03 (s; 1H), 7.89 (s, 1H), 6.69 (s, 2H). MS: m/z 355, 357 (M+H)$^+$.

d) 4-Amino-3-bromo-7-(3,4,5-trimethoxyphenyl)-thieno[3,2-c]pyridine (16)

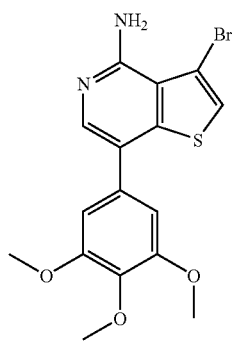

The mixture of 4-amino-3-bromo-7-iodo-[3,2-c]pyridine (1.7 g, 4.85 mmol), Pd(PPh$_3$)$_4$ (560 mg, 10 mol %), 3,4,5-trimethoxybenzeneboronic acid (1.1 g, 5.34 mmol) and 2M sodiumbicarbonate (12 ml, 24.3 mmol) in DME (30 ml) was stirred for 14 hours at 80° C. The crude mixture was directly applied to SCX (Varian, 10 g×3), and eluted with 1N NH$_3$ in CHCl$_3$ and MeOH. The eluant was collected and concentrated in vacuo. The residue was purified by chromatography on a silica gel column to afford 4-amino-3-bromo-7-(3,4,5-trimethoxyphenyl)-thieno[3,2-c]pyridine (1.0 g). 1H NMR (400 MHz, DMSO-d$_6$) ppm 7.97 (s, 1H), 7.85 (s, 1H), 6.89 (s, 2H), 6.64 (s, 2H), 3.83 (s, 6H), 3.71 (s, 3H). MS: m/z 395, 397 (M+H)$^+$.

e) 4-Amino-3-(4-chlorophenyl)-7-(3,4,5-trimethoxyphenyl)-thieno[3,2-c]pyridine (Ip)

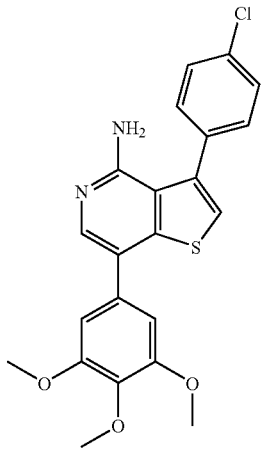

The mixture of 4-amino-3-bromo-7-(3,4,5-trimethoxyphenyl)-thieno[3,2-c]pyridine (30 mg, 0.076 mmol), Pd(PPh$_3$)$_4$ (17 mg, 10 mol %), 4-chlorobenzeneboronic acid (30 mg, 0.19 mmol) and 2M sodium bicarbonate (0.19 ml, 0.38 mmol) in DME (2 ml) was stirred for 14 hours at 80° C. The crude mixture was directly applied to SCX (Varian, 5 g) and eluted with 1N NH$_3$ in CHCl$_3$ and MeOH. The eluant was collected and concentrated in vacuo. The residue was purified by chromatography on a silica gel column to afford the titled compound (15.5 mg) 1H NMR (400 MHz, DMSO-d$_6$) ppm 7.99 (s, 1H), 7.60 (d, J=8.6 Hz, 2H), 7.58 (s, 1H), 7.51 (d, J=7.3 Hz, 2H), 6.95 ((s, 2H), 5.47 (s, 2H), 3.85 (s, 6H), 3.73 (s, 3H). MS: m/z 427, 429 (M+H)$^+$.

Example 12

4-Amino-3-(3-hydroxyphenyl)-7-(3,4,5-trimethoxyphenyl)-thieno[3,2-c]pyridine (Ir)

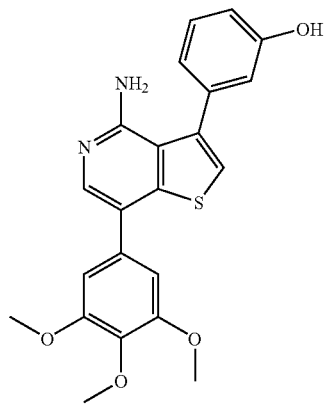

In a similar manner as described in Example 11e, the title compound was obtained from compound 16 and 3-(4,4,5,5-tetramethyl-1,3,2-dioxaborolan-2-yl)phenol as a solid. 1H NMR (400 MHz, DMSO-d$_6$) ppm 9.82 (s, 1H), 7.96 (s, 1H), 7.51 (s, 1H), 7.34 (dd, J=7.8 Hz, 1H), 6.95 (s, 2H), 6.92-6.86 (m, 2H), 6.83-6.82 (m, 1H), 5.57 (s, 2H), 3.85 (s, 6H), 3.72 (s, 3H). MS: m/z 409 (M+H)+.

Example 13

4-Amino-3-(2,4-dichlorophenyl)-7-(3,4,5-trimethoxyphenyl)-thieno[3,2-c]pyridine (Is)

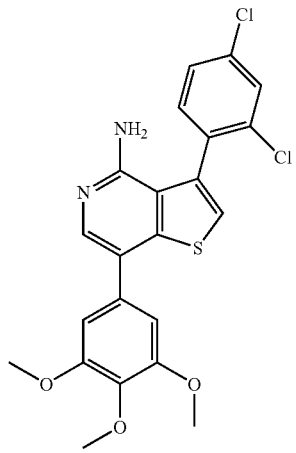

In a similar manner as described in Example 11e, the title compound was obtained from compound 16 and 2,4-dichlorophenylboronic acid as a solid. 1H NMR (400 MHz, DMSO-$d_6$) ppm 7.98 (s, 1H), 7.86 (d, J=2.0 Hz, 1H), 7.62 (s, 1H), 7.60 (dd, J=1.9, 8.2 Hz, 1H), 7.56 (d, J=8.3 Hz, 1H), 6.95 (s, 2H), 5.30 (s, 2H), 3.86 (s, 6H), 3.73 (s, 3H). MS: m/z 461, 463 (M+H)+.

Example 14

4-Amino-3-(3-chloro-4-fluorophenyl)-7-(3,4,5-trimethoxyphenyl)-thieno[3,2-c]pyridine (It)

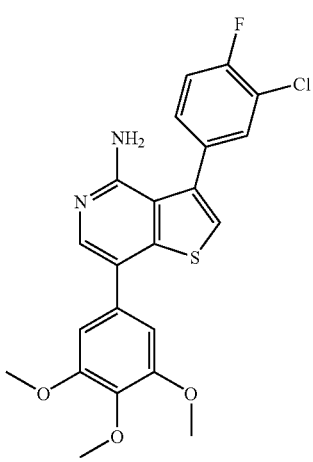

In a similar manner as described in Example 11e, the title compound was obtained from compound 16 and 3-chloro-4-fluorophenylboronic acid as a solid. 1H NMR (400 MHz, DMSO-$d_6$) ppm 7.99 (s, 1H), 7.73 (dd, J=2.1, 7.2 Hz, 1H), 7.63 (s, 1H), 7.57 (dd, J=8.8 Hz, 1H), 7.49 (ddd, J=2.2, 4.7, 8.5 Hz, 1H), 6.94 (s, 2H), 5.52 (s, 2H), 3.85 (s, 6H), 3.72 (s, 3H). MS: m/z 445, 447 (M+H)+.

Example 15

4-Amino-3-(benzo[1,3]-dioxol-5-yl)-7-(3,4,5-trimethoxyphenyl)-thieno[3,2-c]pyridine (Iu)

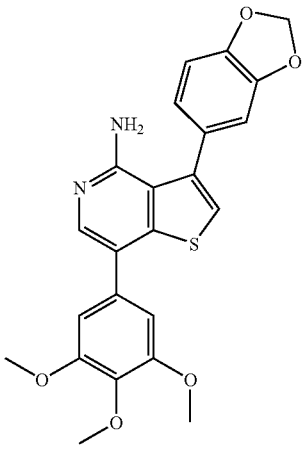

In a similar manner as described in Example 11e, the title compound was obtained from compound 16 and 3,4-methylenedioxyphenyl)boronic acid as a solid. 1H NMR (400 MHz, DMSO-$d_6$) ppm 7.96 (s, 1H), 7.49 (s, 1H), 7.07 (d, J=8.1 Hz, 1H), 7.04 (d, J=1.8 Hz, 1H), 6.94-6.92 (m, 3H), 6.13 (s, 2H), 5.56 (s, 2H), 3.85 (s, 6H), 3.72 (s, 3H). MS: m/z 437 (M+H)+.

Example 16

4-Amino-3-(2-naphtyl)-7-(3,4,5-trimethoxyphenyl)thieno[3,2-c]pyridine

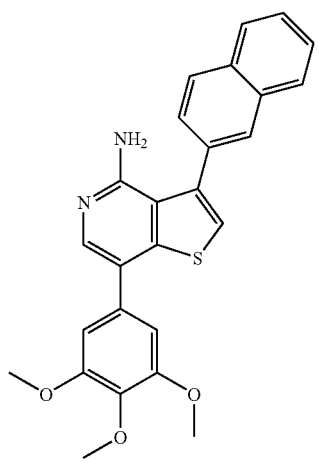

In a similar manner as described in Example 11e, the title compound was obtained from compound 16 and 2-naphthaleneboronic acid as a solid. 1H NMR (400 MHz, DMSO-$d_6$) ppm 8.10-8.02 (m, 4H), 8.00 (s, 1H), 7.65 (s, 1H), 7.63-7.61 (m, 3H), 6.98 (s, 2H), 5.47 (s, 2H), 3.87 (s, 6H), 3.74 (s, 3H). MS: m/z 443 (M+H)+.

Example 17

4-Amino-3-(4-methoxyphenyl)-7-(3,4,5-trimethoxyphenyl)-thieno[3,2-c]pyridine (Iw)

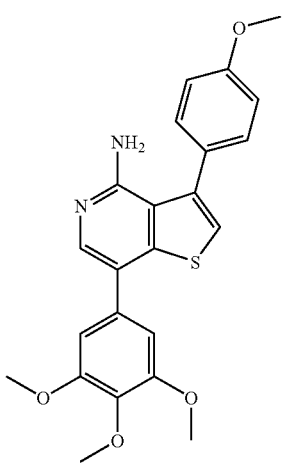

In a similar manner as described in Example 11e, the title compound was obtained from compound 16 and 4-methoxyphenylboronic acid as a solid. 1H NMR (400 MHz, DMSO-$d_6$) ppm 7.96 (s, 1H), 7.47 (s, 1H), 7.41 (d, J=8.8 Hz, 2H), 7.10 (d, J=8.8 Hz, 2H), 6.95 (s, 2H), 5.50 (s, 2H), 3.85 (s, 6H), 3.84 (s, 3H), 3.72 (s, 3H). MS: m/z 423 (M+H)$^+$.

Example 18

4-Amino-3-(3-hydroxymethylphenyl)-7-(3,4,5-trimethoxyphenyl)-thieno[3,2-c]pyridine (Ix)

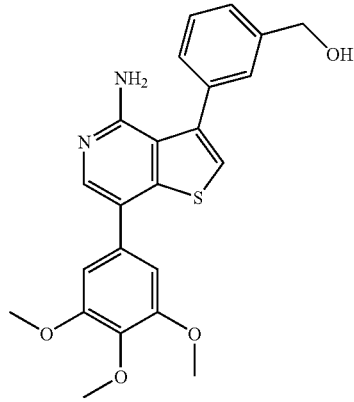

In a similar manner as described in Example 11e, the title compound was obtained from compound 16 and 3-(hydroxymethyl)benzeneboronic acid as a solid. 1H NMR (400 MHz, DMSO-d6) ppm 7.97 (s, 1H), 7.53-7.42 (m, 4H), 7.36-7.33 (m, 1H), 6.96 (s, 2H), 5.49 (s, 2H), 5.36 (t, J=5.8 Hz, 1H), 4.60 (d, J=5.6 Hz, 2H), 3.86 (s, 6H), 3.73 (s, 3H). MS: m/z 423 (M+H)$^+$.

Example 19

4-Amino-3-(2,3-dichlorophenyl)-7-(3,4,5-trimethoxyphenyl)-thieno[3,2-c]pyridine (Iy)

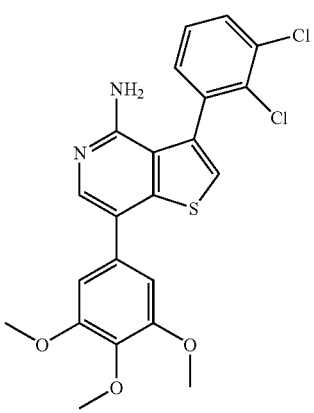

In a similar manner as described in Example 11e, the title compound was obtained from compound 16 and 2,3-dichlorophenylboronic acid as a solid. 1H NMR (400 MHz, DMSO-$d_6$) ppm 7.98 (s, 1H), 7.84-7.80 (m, 1H), 7.65 (s, 1H), 7.55-7.52 (m, 2H), 6.96 (s, 2H), 5.28 (s, 2H), 3.86 (s, 6H), 3.73 (s, 3H). MS: m/z 461, 463 (M+H)$^+$.

Example 20

4-Amino-3 (1H-Indol-5-yl)-7-(3,4,5-trimethoxyphenyl)-thieno[3,2-c]pyridine (Iaa)

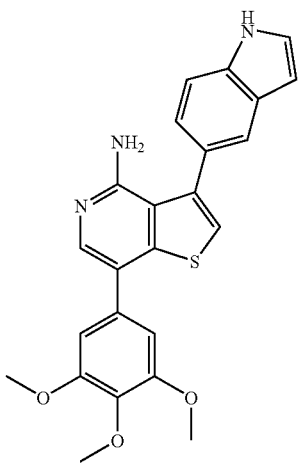

In a similar manner as described in Example 11e, the title compound was obtained from compound 16 and 5-indolyl boronic acid as a solid. 1H NMR (400 MHz, DMSO-$d_6$) ppm 11.35 (s, 1H), 7.95 (s, 1H), 7.63 (m, 1H), 7.55 (d, J=8.3 Hz, 1H), 7.48 (dd, J=2.8 Hz, 1H), 7.45 (s, 1H), 7.16 (dd, J=1.6, 8.2 Hz, 1H), 6.97 (s, 2H), 6.53-6.52 (m, 1H), 5.49 (s, 2H), 3.86 (s, 6H), 3.73 (s, 3H). MS: m/z 432 (M+H)$^+$.

Example 21

4-Amino-3-(4-(Cyclopentanecarbonyl-amino)-phenyl)-7-(3,4,5-trimethoxyphenyl)-thieno[3,2-c]pyridine (Iab)

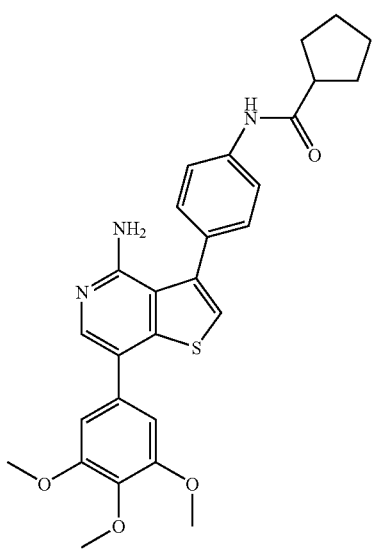

In a similar manner as described in Example 11e, the title compound was obtained from compound 16 and cyclopentanecarboxylic acid [4-(4,4,5,5-tetramethyl-[1,3,2]dioxaborolan-2-yl)-phenyl]-amide as a solid. 1H NMR (400 MHz, DMSO-d$_6$) ppm 10.10 (s, 1H), 7.96 (s, 1H), 7.77 (d, J=8.6 Hz, 2H), 7.48 (s, 1H), 7.40 (d, J=8.6 Hz, 2H), 6.95 (s, 2H), 5.49 (s, 2H), 3.85 (s, 6H), 3.72 (s, 3H), 2.85-2.78 (m, 1H), 1.91-1.55 (m, 8H). MS: m/z 504 (M+H)$^+$.

Example 22

4-Amino-3-(2-methyl-benzothiazol-5-yl)-7-(3,4,5-trimethoxyphenyl)-thieno[3,2-c]pyridine (Iac)

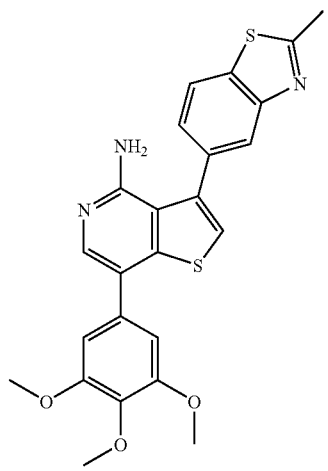

In a similar manner as described in Example 11e, the title compound was obtained from compound 16 and 5-(5,5-Dimethyl-[1,3,2]dioxaborinane-2-yl)-2-methyl-benzothiazole as a solid. 1H NMR (400 MHz, DMSO-d$_6$) ppm 8.20 (d, J=8.1 Hz, 1H), 7.99 (2H), 7.62 (s, 1H), 7.50 (dd, J=1.6, 8.2 Hz, 1H), 6.97 (s, 2H), 5.46 (s, 2H), 3.86 (s, 6H), 3.73 (s, 3H), 2.85 (s, 3H). MS: m/z 464 (M+H)$^+$.

Example 23

4-Amino-3-(4-acetylphenyl)-7-(3,4,5-trimethoxyphenyl)-thieno[3,2-c]pyridine (Iad)

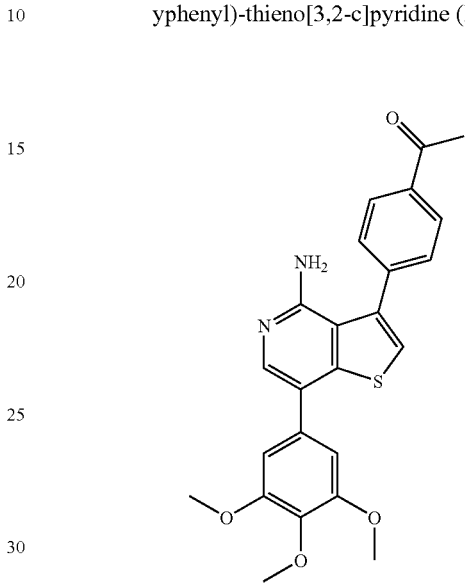

In a similar manner as described in Example 11e, the title compound was obtained from compound 16 and 4-acetylphenylboronic acid as a solid. 1H NMR (400 MHz, DMSO-d$_6$) ppm 8.11 (d, J=8.3 Hz, 2H), 8.01 (s, 1H), 7.65 (d, J=8.3 Hz, 2H), 7.64 (s, 1H), 6.96 (s, 2H), 5.49 (s, 2H), 3.86 (s, 6H), 3.73 (s, 3H), 2.66 (s, 3H). MS: m/z 435 (M+H)$^+$.

Utility of the Present Invention

The following biological data clearly show that the present compounds are useful for treating or preventing diseases or conditions caused by inappropriate vasculogenesis, angiogenesis, vessel maturation or cell motility mediated by the imbalance or inappropriate activity of one or more tyrosine kinases selected from the group consisting of Tie-2, VEGFR-2, Src-c and EphB4 proteins, Including but not limited to, cancer and atherosclerosis.

BIOLOGICAL DATA

EphB4 Enzyme Assay

The EphB4 enzyme assay used Scintillation Proximity Assay technology to measure enzyme activity. This method measured the ability of the purified enzymes to catalyse the transfer of the γ-phosphate from ATP onto tyrosine residues in a biotinylated synthetic peptide. The peptide used for the EphB4 enzyme activity assay was biotin-Ahx-MAHFENY-EFFHAKKK-CONH2. (SEQ ID NO:1) The enzyme used was GST-EphB4, baculovirus expressed recombinant constructs of the intracellular domains of human EphB4 (amino acids 600-914, BR # 21454) tagged by GST. Peptide phosphorylation was detected using the following procedure: for enzyme preactivation, 7.4 uM GST-EphB4 was incubated for 30 mins at room temperature with 50 uM ATP and 10 mM MgCl$_2$ in 30 mM HEPES buffer (pH7.4). Preactivated GST- EphB4 was incubated then for 3 hours at room temperature in 96 well plates with 6 uM peptide, 1 uM ATP, 10 mM MgCl$_2$, 0.1 mg/ml BSA, 5 uCi/ml P33, 1 mM DTT, 1 mM CHAPS, 5 mM KCl and 23-25 uM test compound in 100 mM HEPES (pH7.4). Each reaction was stopped by the addition of 0.1 mg Streptavidin SPA beads in 100 mM EDTA/1×PBS, pH 7.2. The signal was measured using a Wallac Trilux scintillation counter (Wallac). The percent inhibition of activity was calculated relative to positive (C1) and negative (C2) control wells using, 100*(1−(U1−C2)/(C1−C2)). The concentration of test compound was determined using the equation, y=((Vmax*x)/(K+x))+Y2, where "K" was equal to the IC50. The IC50 values were converted to pIC50 values, i.e., −log IC50 in Molar concentration. The results for some representative compounds are shown below in Table 1.

TABLE 1

| Example No. compounds | pIC$_{50}$ values |
|---|---|
| Id | ++++ |
| Ib | +++ |
| Il | ++ |
| Ig | + |

Legend
| pIC$_{50}$ values | Symbol |
|---|---|
| 8.5-9.50 | ++++ |
| 7.5-8.49 | +++ |
| 6.5-7.49 | ++ |
| 5.5-6.49 | + |
| pIC$_{50}$ = −log$_{10}$(IC$_{50}$) | |

TIE-2 Enzyme Assay

The TIE-2 enzyme assay used the LANCE method (Wallac) and GST-TIE2, baculovirus expressed recombinant constructs of the intracellular domains of human TIE2 (amino acids 762-1104, GenBank Accession # L06139) tagged by GST). The method measured the ability of the purified enzymes to catalyse the transfer of the γ-phosphate from ATP onto tyrosine residues in a biotinylated synthetic peptide, D1-15 (biotin-C6-LEARLVAYEGWVAGKKKamide). This peptide phosphorylation was detected using the following procedure: for enzyme preactivation, GST-TIE2 was incubated for 30 mins at room temperature with 2 mM ATP, 5 mM MgCl2 and 12.5 mM DTT in 22.5 mM HEPES buffer (pH7.4). Preactivated GST-TIE2 was incubated for 30 mins at room temperature in 96 well plates with 1 uM D1-15 peptide, 80 uM ATP, 10 mM MgCl$_2$, 0.1 mg/ml BSA and the test compound (diluted from a 10 mM stock in DMSO, final DMSO concentration was 2.4%) In 1 mM HEPES (pH7.4). The reaction was stopped by the addition of EDTA (final concentration 45 mM). Streptavidin linked-APC (allophycocyanin, Molecular Probe) and Europium-labeled anti-phosphorylated tyrosine antibody (Wallac) were then added at the final concentration of 17 ug/well and 2.1 ug/well, respectively. The APC signal was measured using an ARVO multilabel counter. (Wallac Berthold Japan). The percent inhibition of activity was calculated relative to blank control wells. The concentration of test compound that inhibits 50% of activity (IC50) was interpolated using nonlinear regression (Levernberg-Marquardt) and the equation, y=Vmax (1−x/(K+x))+Y2, where "K" was equal to the IC50. The IC50 values were converted to pIC50 values, i.e., −log IC50 in Molar concentration. The results for some representative compounds are shown below in Table 2.

TABLE 2

| Example No. compounds | pIC$_{50}$ values |
|---|---|
| Id | +++ |
| Ib | ++ |
| Iaa | + |

Legend
| pIC$_{50}$ values | Symbol |
|---|---|
| 8.0-9.0 | +++ |
| 7.0-7.99 | ++ |
| 6.0-6.99 | + |
| pIC$_{50}$ = −log$_{10}$(IC$_{50}$) | |

VEGFR-2 Enzyme Assay

The VEGF enzyme assay used the LANCE method (Wallac) and GST-VEGFR2, baculovirus expressed recombinant constructs of the intracellular domains of human TIE2 tagged by GST. The method measured the ability of the purified enzymes to catalyse the transfer of the γ-phosphate from ATP onto tyrosine residues in a biotinylated synthetic peptide, (biotin-aminohexyl-EEEEYFELVAKKKK-NH$_2$, SEQ ID NO:2). This peptide phosphorylation was detected using the following procedure: GST-VEGFR2 was incubated for 40-60 mins at room temperature with 75 uM ATP, 5 mM MgCl2, 0.1 mM DTT, 0.1 mg/mL BSA and the test compound (diluted from a 10 mM stock in DMSO for desired concentration) in 100 mM HEPES buffer. The reaction was stopped by the addition of EDTA (final concentration 50 mM). Streptavidin linked-APC (allophycocyanin, Molecular Probe) and Europium-labeled anti-phosphorylated tyrosine antibody (Wallac) were then added at the final concentration of 15 nM and 1 nM, respectively. The APC signal was measured using an ARVO multilabel counter (Wallac Berthold, Japan). The percent inhibition of activity was calculated relative to blank control wells. The concentration of test compound that inhibits 50% of activity (IC50) was interpolated using nonlinear regression (Levernberg-Marquardt) and the equation, y=Vmax (1−x/(K+x))+Y2, where "K" was equal to the IC50. The IC50 values were converted to pIC50 values, i.e., −log IC50 in Molar concentration. The results for some representative compounds are shown below in Table 3.

TABLE 3

| Example No. compounds | pIC$_{50}$ values |
|---|---|
| Ie | +++ |
| Ib | ++ |
| Ia | + |

Legend
| pIC$_{50}$ values | Symbol |
|---|---|
| 8.5-9.5 | +++ |
| 7.5-8.49 | ++ |
| 6.5-7.49 | + |
| pIC$_{50}$ = −log$_{10}$(IC$_{50}$) | |

Src Enzyme Assay

Assay Principle:

The Src enzyme assay used Homogeneous Time Resolved Fluorescence (HTRF) assay technology to measure the enzyme activity. HTRF is based on fluorescence resonance energy transfer between a Europium-labeled phospho-tyrosine antibody (donor) and Allophycocyanin (APC) conjugated to streptavidin (acceptor). This method measured the ability of the purified enzymes to catalyze the transfer of the γ-phosphate from ATP onto tyrosine residues in a biotinylated synthetic peptide. The peptide used for the Src enzyme activity assay was biotin-(6-amino caproic acid)-AAAQQIYGQI-NH2. The enzyme used was baculovirus expressed N-85 Src with the deletion of first 85 amino acids, which precede the first globular domain (amino acids 86-536, BR# 455).

Assay Protocol:

To preactivate enzyme, 180 µM N-85 Src was incubated with 5 mM ATP and 50 mM $MgCl_2$ for 40 min on ice. The preactivated enzyme (0.4 nM final concentration) was then incubated for 30 min at room temperature in either 96-well or 384-well plates containing 200 nM peptide, 10 µM ATP, 0.05 mg/ml $MgCl_2$, and test compound in 0.1 M HEPES pH 7.5. Each reaction was first stopped by the addition of 45 mM EDTA in 0.1 M HEPES pH7.5, then, HTRF reagent was added to measure the signal. After 10 min incubation at room temperature, the plates were read at 665 nm on a Wallac Victor reader with a time delay. The percent inhibition of activity was calculated relative to positive (C1) and negative (C2, EDTA added) control wells using, 100*(1−(U1−C2)/(C1−C2)). The concentration of test compound yielding 50% inhibition was determined using the equation, y=((Vmax*x)/(K+x))+Y2, where "K" was equal to the IC50. The IC50 values were converted to pIC50 values, i.e., −log IC50 in Molar concentration. The results for some representative compounds are shown below in Table 4.

TABLE 4

| Example No. compounds | pIC$_{50}$ values |
|---|---|
| Id | +++ |
| Ia | ++ |
| Ib | + |

Legend

| pIC$_{50}$ values | Symbol |
|---|---|
| 8.0-9.0 | +++ |
| 7.0-7.99 | ++ |
| 6.0-6.99 | + | pIC$_{50}$ = −log$_{10}$(IC$_{50}$)

What is claimed is:

1. A compound selected from the group consisting of:
(a) 4-amino-3-(4-((2-fluoro-5-(trifluoromethyl)aminocarbonylamino)phenyl)-7-(3-chlorophenyl)-furo[3,2-c]pyridine;
(b) 4-amino-3-(4-((2-fluoro-5-(trifluoromethyl)aminocarbonylamino)phenyl)-furo[3,2-c]pyridine;
(c) 4-amino-3-(4-((2-fluoro-5-(trifluoromethyl)aminocarbonylamino)phenyl)-7-bromo-furo[3,2-c]pyridine;
(d) 4-amino-3-(4-((2-fluoro-5-(trifluoromethyl)aminocarbonylamino)phenyl)-7-(3-sulfamoylphenyl)-furo[3,2-c]pyridine;
(e) 4-amino-3-(4-((2-fluoro-5-(trifluoromethyl)aminocarbonylamino)phenyl)-7-(3-pyridyl)-furo[3,2-c]pyridine;
(f) 4-amino-3-(3-chloro-4-fluoro-phenyl)-7-(3-sulfamoylphenyl)-thieno[3,2-c]pyridine;
(g) 4-amino-3-(3-chloro-4-fluoro-phenyl)thieno[3,2-c]pyridine;
(h) 4-amino-7-bromo-3-(3-chloro-4-fluoro-phenyl)thieno[3,2-c]pyridine;
(i) 4-amino-3-(3-chloro-4-fluoro-phenyl)-7-(3-sulfamoylphenyl)thieno[3,2-c]pyridine;
(j) 4-amino-3-(3-chloro-4-fluoro-phenyl)-7-(3-acetamidephenyl)thieno[3,2-c]pyridine;
(k) 4-amino-3-(3-chloro-4-fluoro-phenyl)-7-(3-pyridyl)-thieno[3,2-c]pyridine;
(l) 4-amino-3-(3-chloro-4-fluoro-phenyl)-7-(3-methansulfonylphenyl)thieno-[3,2-c]pyridine;
(m) 4-amino-3-(3-chloro-4-fluoro-phenyl)-7-(3-cyanophenyl)-thieno[3,2-c]pyridine;
(n) 4-amino-3-(3-chloro-4-fluoro-phenyl)-7-(3-acetylphenyl)-thieno[3,2-c]pyridine;
(o) 4-amino-3-(3-hydroxyphenyl)-thieno[3,2-c]pyridine;
(p) 4-amino-3-(4-chlorophenyl)-7-(3,4,5-trimethoxyphenyl)-thieno[3,2-c]pyridine;
(q) 4-amino-3-(4-chlorophenyl)-7-(3,4,5-trimethoxyphenyl)-thieno[3,2-c]pyridine;
(r) 4-amino-3-(3-hydroxyphenyl)-7-(3,4,5-trimethoxyphenyl)-thieno[3,2-c]pyridine;
(s) 4-amino-3-(2,4-dichlorophenyl)-7-(3,4,5-trimethoxyphenyl)-thieno[3,2-c]pyridine;
(t) 4-amino-3-(3-chloro-4-fluorophenyl)-7-(3,4,5-trimethoxyphenyl)-thieno[3,2-c]pyridine;
(u) 4-amino-3-(benzo[1,3]-dioxol-5-yl)-7-(3,4,5-trimethoxyphenyl)-thieno[3,2-c]pyridine;
(v) 4-amino-3-(2-naphtyl)-7-(3,4,5-trimethoxyphenyl)-thieno[3,2-c]pyridine;
(w) 4-amino-3-(4-methoxyphenyl)-7-(3,4,5-trimethoxyphenyl)-thieno[3,2-c]pyridine;
(x) 4-amino-3-(3-hydroxymethylphenyl)-7-(3,4,5-trimethoxyphenyl)-thieno[3,2-c]pyridine;
(y) 4-amino-3-(2,3-dichlororphenyl)-7-(3,4,5-trimethoxyphenyl)-thieno[3,2-c]pyridine;
(z) 4-amino-3-(1H-indol-5-yl)-7-(3,4,5-trimethoxyphenyl)-thieno[3,2-c]pyridine.
(aa) 4-amino-3-(4-(cyclopentanecarbonyl-amino)-phenyl)-7-(3,4,5-trimethoxyphenyl)-thieno[3,2-c]pyridine;
(ab) ino-3-(2-methyl-benzothiazol-5-yl)-7-(3,4,5-trimethoxyphenyl)-thieno[3,2-c]pyridine; and
(ac) 4-amino-3-(4-acetylphenyl)-7-(3,4,5-trimethoxyphenyl)-thieno[3,2-c]pyridine or salts thereof.

2. A pharmaceutical composition including a therapeutically effective amount of at least one compound of claim 1 and one or more of pharmaceutically acceptable carriers, diluents and excipients.

* * * * *